(12) United States Patent
Mookkan et al.

(10) Patent No.: US 9,555,093 B2
(45) Date of Patent: Jan. 31, 2017

(54) UNIVERSAL VACCINE AGAINST H5N1 LINEAGES

(75) Inventors: Prabakaran Mookkan, Singapore (SG); Fang He, Singapore (SG); Hwei-Sing Jimmy Kwang, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 13/695,591

(22) PCT Filed: Feb. 9, 2011

(86) PCT No.: PCT/SG2011/000059
§ 371 (c)(1),
(2), (4) Date: Oct. 31, 2012

(87) PCT Pub. No.: WO2011/136738
PCT Pub. Date: Nov. 3, 2011

(65) Prior Publication Data
US 2013/0052223 A1  Feb. 28, 2013

Related U.S. Application Data

(60) Provisional application No. 61/329,802, filed on Apr. 30, 2010.

(51) Int. Cl.
*A61K 39/12* (2006.01)
*A61P 31/16* (2006.01)
*A61K 39/145* (2006.01)
*A61K 39/00* (2006.01)

(52) U.S. Cl.
CPC ........... *A61K 39/145* (2013.01); *A61K 39/12* (2013.01); *A61K 2039/5252* (2013.01); *A61K 2039/5256* (2013.01); *A61K 2039/53* (2013.01); *A61K 2039/55566* (2013.01); *A61K 2039/70* (2013.01); *C12N 2710/14143* (2013.01); *C12N 2760/16134* (2013.01)

(58) Field of Classification Search
CPC .............................. C07K 39/00; A61K 39/00
See application file for complete search history.

(56) References Cited

U.S. PATENT DOCUMENTS

| 7,981,428 B2 * | 7/2011 | Wong et al. ............... 424/186.1 |
| 2010/0041740 A1 | 2/2010 | Wong et al. |
| 2011/0020391 A1 | 1/2011 | Süzer et al. |

FOREIGN PATENT DOCUMENTS

| EP | 1925318 A1 | 5/2008 |
| JP | 2010-510281 A | 4/2010 |
| WO | 2009092038 A1 | 7/2009 |
| WO | 2010077986 A2 | 7/2010 |

OTHER PUBLICATIONS

Prabakaran et al. (Journal of Virology, published online in Jan. 2010, vol. 84, p. 3201-3209).*
Prabakaran et al. (Virology, 2008, vol. 380, p. 412-420).*
Carter, N.J. et al., "Prepandemic Influenza Vaccine H5N1 (Split Virion, Inactivated, Adjuvanted) [Prepandrix™]," A Review of its Use as an Active Immunization Against Influenza A Subtype H5N1 Virus, Biodrugs 2008, vol. 22, No. 5, pp. 279-292, © 2008 Adis Drug Evaluation.
Ichinohe, T. et al., "Cross-Protection Against H5N1 Influenza Virus Infection is Afforded by Intranasal Inoculation with Seasonal Trivalent Inactivated Influenza Vaccine," The Journal of Infectious Diseases 2007, vol. 196, pp. 1313-1320.
Lerouox-Roels, I. et al., "Priming with AS03 A-Adjuvanted H5N1 Influenza Vaccine Improves the Kinetics, Magnitude and Durability of the Immune Response After a Heterologous Booster Vaccination: An Open-Non-Randomised Extension of a Double-Blind Randomised Primary Study," Vaccine, vol. 28, pp. 849-857, Jan. 8, 2010, © 2009 Elsevier Ltd.
Lerouox-Roels, I. et al., "Broad Clade 2 Cross-Reactive Immunity Induced by an Adjuvanted Clade 1 rH5N1 Pandemic Influenza Vaccine," PloS one, vol. 3, No. 2, e1665 pp. 1-5.
Forrest, H.L. et al., "Single- and multiple-clade influenza A H5N1 vaccines induce cross-protection in ferrets," Vaccine, Elsevier LTD., GB, vol. 27, No. 31, Jun. 24, 2009, pp. 4187-4195.
Gerhard, W. et al., "Prospects for universal influenza virus vaccine," Emerging Infectious Diseases, vol. 12, No. 4, Apr. 2006, pp. 569-574, XP-002711940.
Kaverin, N.V. et al., "Epitope mapping of the hemagglutinin molecular of a highly pathogenic H5N1 influenza virus by using monoclonal antibodies," Journal of Virology, vol. 81, No. 23, Dec. 2007, pp. 12911-12917, XP-002711941.
Mookkan, P. et al., "Neutralizing epitopes of influenza virus hemagglutinin: Target for the development of a universal vaccine against H5N1 lineages," Journal of Virology, vol. 84, No. 22, Nov. 15, 2010, pp. 11822-11830.
EP Communication dated Sep. 10, 2013, Application No. 11775384.8-1403 / 2563389 PCT/SG2011/000059, Applicant: TEMASEK Life Sciences Laboratory Limited, Supplementary European Search Report, 7 pages.
Japanese Office Action, Application No. 2013-507923, Nov. 10, 2014, 3 pages.

* cited by examiner

*Primary Examiner* — Agnieszka Boesen
(74) *Attorney, Agent, or Firm* — Rothwell, Figg, Ernst & Manbeck, P.C.

(57) ABSTRACT

The present invention relates to a universal H5N1 vaccine. More specifically, the present invention relates to the identification of three H5N1 strains which cover the entire variants in the neutralizing epitopes of hemagglutinin among most H5N1 lineages. The present invention further relates a universal H5N1 vaccine that comprises the three H5N1 strains or that comprises hemagglutinin peptides of each of these three strains.

10 Claims, 6 Drawing Sheets

SEQUENCE LISTING

```
<160> NUMBER OF SEQ ID NOS: 11

<210> SEQ ID NO 1
<211> LENGTH: 30
<212> TYPE: DNA
<213> ORGANISM: Influenza A virus

<400> SEQUENCE: 1
acgcgtcgac atggagaaaa tagtgcttct                                          30

<210> SEQ ID NO 2
<211> LENGTH: 34
<212> TYPE: DNA
<213> ORGANISM: Influenza A virus

<400> SEQUENCE: 2
ataaggcggc cgcttaaatg caaattctgc attg                                     34
```

```
<210> SEQ ID NO 3
<211> LENGTH: 1707
<212> TYPE: DNA
<213> ORGANISM: Influenza A virus
<220> FEATURE:

```
gtc aag aaa ggg gac tca gca att atg aaa agt gaa ttg gaa tat ggt        864
Val Lys Lys Gly Asp Ser Ala Ile Met Lys Ser Glu Leu Glu Tyr Gly
            275                 280                 285 aac tgc aac acc aag tgt caa act cca atg ggg gcg ata aac tct agt        912
Asn Cys Asn Thr Lys Cys Gln Thr Pro Met Gly Ala Ile Asn Ser Ser
        290                 295                 300 atg cca ttc cac aac ata cac cct ctc acc atc ggg gaa tgc ccc aaa        960
Met Pro Phe His Asn Ile His Pro Leu Thr Ile Gly Glu Cys Pro Lys
305                 310                 315                 320 tat gtg aaa tca aac aga tta gtc ctt gca aca ggg ctc aga aat agc       1008
Tyr Val Lys Ser Asn Arg Leu Val Leu Ala Thr Gly Leu Arg Asn Ser
                325                 330                 335 cct caa aga gag agc aga aga aag aga gga cta ttt gga gct ata           1056
Pro Gln Arg Glu Ser Arg Arg Lys Arg Gly Leu Phe Gly Ala Ile
            340                 345                 350 gca ggt ttt ata gag gga gga tgg cag gga atg gta gat ggc tgg tat       1104
Ala Gly Phe Ile Glu Gly Gly Trp Gln Gly Met Val Asp Gly Trp Tyr
            355                 360                 365 ggg tac cac cat agc aat gag cag ggg agt ggg tac gct gca gac aaa       1152
Gly Tyr His His Ser Asn Glu Gln Gly Ser Gly Tyr Ala Ala Asp Lys
        370                 375                 380 gaa tcc act caa aag gca ata gat gga gtc acc aat aag gtc aac tca       1200
Glu Ser Thr Gln Lys Ala Ile Asp Gly Val Thr Asn Lys Val Asn Ser
385                 390                 395                 400 att att gac aaa atg aac act cag ttt gag gct gtt gga agg gaa ttt       1248
Ile Ile Asp Lys Met Asn Thr Gln Phe Glu Ala Val Gly Arg Glu Phe
                405                 410                 415 aat aac tta gaa agg aga ata gag aat tta aac aag aag atg gaa gac       1296
Asn Asn Leu Glu Arg Arg Ile Glu Asn Leu Asn Lys Lys Met Glu Asp
            420                 425                 430 ggg ttt cta gat gtt tgg act tat aat gcc gaa ctt ctg gtt ctc atg       1344
Gly Phe Leu Asp Val Trp Thr Tyr Asn Ala Glu Leu Leu Val Leu Met
        435                 440                 445 gaa aat gag aga act cta gac ttt cat gac tca aat gtt aag aac ctc       1392
Glu Asn Glu Arg Thr Leu Asp Phe His Asp Ser Asn Val Lys Asn Leu
450                 455                 460 tac gac aag gtc cga cta cag ctt agg gat aat gca aaa gag ctg ggt       1440
Tyr Asp Lys Val Arg Leu Gln Leu Arg Asp Asn Ala Lys Glu Leu Gly
465                 470                 475                 480 aac ggt tgt ttc gag ttc tat cac aaa tgt gat aat gaa tgt atg gaa       1488
Asn Gly Cys Phe Glu Phe Tyr His Lys Cys Asp Asn Glu Cys Met Glu
                485                 490                 495 agt ata aga aac gga acg tac aac tat ccg cag tat tca gaa gaa gca       1536
Ser Ile Arg Asn Gly Thr Tyr Asn Tyr Pro Gln Tyr Ser Glu Glu Ala
            500                 505                 510 aga tta aaa aga gag gaa ata agt ggg gta aaa ttg gaa tca ata gga       1584
Arg Leu Lys Arg Glu Glu Ile Ser Gly Val Lys Leu Glu Ser Ile Gly
        515                 520                 525 act tac caa ata ctg tca att tat tca aca gta gcg agt tcc cta gca       1632
Thr Tyr Gln Ile Leu Ser Ile Tyr Ser Thr Val Ala Ser Ser Leu Ala
530                 535                 540 ctg gca atc atg ata gct ggt cta tct tta tgg atg tgc tcc aat gga       1680
Leu Ala Ile Met Ile Ala Gly Leu Ser Leu Trp Met Cys Ser Asn Gly
545                 550                 555                 560 tcg tta caa tgc aga att tgc att taa                                   1707
Ser Leu Gln Cys Arg Ile Cys Ile
                565
```

<210> SEQ ID NO 4

<211> LENGTH: 568
<212> TYPE: PRT
<213> ORGANISM: Influenza A virus
<220> FEATURE:
<221> NAME/KEY: misc_feature
<222> LOCATION: (5)..(5)
<223> OTHER INFORMATION: The 'Xaa' at location 5 stands for Val.

<400> SEQUENCE: 4

```
Met Glu Lys Ile Xaa Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Ala Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365
```

```
Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
        530                 535                 540

Leu Ala Ile Met Ile Ala Gly Leu Ser Leu Trp Met Cys Ser Asn Gly
545                 550                 555                 560

Ser Leu Gln Cys Arg Ile Cys Ile
                565

<210> SEQ ID NO 5
<211> LENGTH: 1695
<212> TYPE: DNA
<213> ORGANISM: Influenza A virus
<220> FEATURE:
<221> NAME/KEY: CDS
<222> LOCATION: (1)..(1695)

<400> SEQUENCE: 5 atg gag aaa ata gtg ctt ctt ttt gca ata gtc agt ctt gtt aaa agt    48
Met Glu Lys Ile Val Leu Leu Phe Ala Ile Val Ser Leu Val Lys Ser
1               5                   10                  15 gat cag att tgc att ggt tac cat gca aac aac tcg aca gag cag gtt    96
Asp Gln Ile Cys Ile Gly Tyr His Ala Asn Asn Ser Thr Glu Gln Val
                20                  25                  30 gac aca ata atg gaa aag aac gtt act gtt aca cat gcc caa gac ata   144
Asp Thr Ile Met Glu Lys Asn Val Thr Val Thr His Ala Gln Asp Ile
            35                  40                  45 ctg gaa aag aaa cac aac ggg aag ctc tgc gat cta gat gga gtg aag   192
Leu Glu Lys Lys His Asn Gly Lys Leu Cys Asp Leu Asp Gly Val Lys
        50                  55                  60 cct cta att ttg aga gat tgt agc gta gct gga tgg ctc ctc gga aac   240
Pro Leu Ile Leu Arg Asp Cys Ser Val Ala Gly Trp Leu Leu Gly Asn
65                  70                  75                  80 cca atg tgt gac gaa ttc atc aat gtg ccg gaa tgg tct tac ata gtg   288
Pro Met Cys Asp Glu Phe Ile Asn Val Pro Glu Trp Ser Tyr Ile Val
                85                  90                  95 gag aag gcc aat cca gtc aat gac ctc tgt tac cca ggg gat ttc aat   336
Glu Lys Ala Asn Pro Val Asn Asp Leu Cys Tyr Pro Gly Asp Phe Asn
                100                 105                 110 gac tat gaa gaa ttg aaa cac cta ttg agc aga ata aac cat ttt gag   384
```

```
                Asp Tyr Glu Glu Leu Lys His Leu Leu Ser Arg Ile Asn His Phe Glu
                            115                 120                 125 aaa att cag atc atc ccc aaa agt tct tgg tcc agt cat gaa gcc tca         432
Lys Ile Gln Ile Ile Pro Lys Ser Ser Trp Ser Ser His Glu Ala Ser
130                 135                 140 tta ggg gtg agc tca gca tgc cca tac cag gga aag tcc tcc ttt ttc         480
Leu Gly Val Ser Ser Ala Cys Pro Tyr Gln Gly Lys Ser Ser Phe Phe
145                 150                 155                 160 aga aat gtg gta tgg ctt atc aac aag aac agt aca tac cca aca ata         528
Arg Asn Val Val Trp Leu Ile Asn Lys Asn Ser Thr Tyr Pro Thr Ile
                    165                 170                 175 aag agg agc tac aat aat acc aac caa gaa gat ctt ttg gta ctg tgg         576
Lys Arg Ser Tyr Asn Asn Thr Asn Gln Glu Asp Leu Leu Val Leu Trp
                180                 185                 190 ggg att cac cat cct aat gat gcg gca gag cag aca aag ctc tat caa         624
Gly Ile His His Pro Asn Asp Ala Ala Glu Gln Thr Lys Leu Tyr Gln
            195                 200                 205 aac cca acc acc tat att tcc gtt ggg aca tca aca cta aac cag aga         672
Asn Pro Thr Thr Tyr Ile Ser Val Gly Thr Ser Thr Leu Asn Gln Arg
        210                 215                 220 ttg gta cca aga ata gct act aga tcc aaa gta aac ggg caa agt gga         720
Leu Val Pro Arg Ile Ala Thr Arg Ser Lys Val Asn Gly Gln Ser Gly
225                 230                 235                 240 agg atg gag ttc ttc tgg aca att tta aag ccg aat gat gca atc aac         768
Arg Met Glu Phe Phe Trp Thr Ile Leu Lys Pro Asn Asp Ala Ile Asn
                    245                 250                 255 ttc gag agt aat gga aat ttc att gct cca gaa tat gca tac aaa att         816
Phe Glu Ser Asn Gly Asn Phe Ile Ala Pro Glu Tyr Ala Tyr Lys Ile
                260                 265                 270 gtc aag aaa ggg gac tca aca att atg aaa agt gaa ttg gaa tat ggt         864
Val Lys Lys Gly Asp Ser Thr Ile Met Lys Ser Glu Leu Glu Tyr Gly
            275                 280                 285 aac tgc aac acc aag tgt caa act cca atg ggg gcg ata aac tct agc         912
Asn Cys Asn Thr Lys Cys Gln Thr Pro Met Gly Ala Ile Asn Ser Ser
        290                 295                 300 atg cca ttc cac aat ata cac cct ctc acc att ggg gaa tgc ccc aaa         960
Met Pro Phe His Asn Ile His Pro Leu Thr Ile Gly Glu Cys Pro Lys
305                 310                 315                 320 tat gtg aaa tca aac aga tta gtc ctt gcg act ggg ctc aga aat agc         1008
Tyr Val Lys Ser Asn Arg Leu Val Leu Ala Thr Gly Leu Arg Asn Ser
                    325                 330                 335 cct caa cga gag acg cga gga tta ttt gga gct ata gca ggt ttt ata         1056
Pro Gln Arg Glu Thr Arg Gly Leu Phe Gly Ala Ile Ala Gly Phe Ile
                340                 345                 350 gag gga gga tgg cag gga atg gta gat ggt tgg tat ggg tac cac cat         1104
Glu Gly Gly Trp Gln Gly Met Val Asp Gly Trp Tyr Gly Tyr His His
            355                 360                 365 agc aat gag cag ggg agt ggg tac gct gca gac aaa gaa tcc act caa         1152
Ser Asn Glu Gln Gly Ser Gly Tyr Ala Ala Asp Lys Glu Ser Thr Gln
        370                 375                 380 aag gca ata gat gga gtc acc aat aag gtc aac tcg atc att gac aaa         1200
Lys Ala Ile Asp Gly Val Thr Asn Lys Val Asn Ser Ile Ile Asp Lys
385                 390                 395                 400 atg aac act cag ttt gag gcc gtt gga agg gaa ttt aac aac tta gaa         1248
Met Asn Thr Gln Phe Glu Ala Val Gly Arg Glu Phe Asn Asn Leu Glu
                    405                 410                 415 agg aga ata gag aat tta aac aag aag atg gaa gac ggg ttc cta gat         1296
Arg Arg Ile Glu Asn Leu Asn Lys Lys Met Glu Asp Gly Phe Leu Asp
                420                 425                 430
```

```
gtc tgg act tat aat gct gaa ctt ctg gtt ctc atg gaa aat gag aga      1344
Val Trp Thr Tyr Asn Ala Glu Leu Leu Val Leu Met Glu Asn Glu Arg
        435                 440                 445 act cta gac ttt cat gac tca aat gtc aag aac ctt tac gac aag gtc      1392
Thr Leu Asp Phe His Asp Ser Asn Val Lys Asn Leu Tyr Asp Lys Val
450                 455                 460 cga cta cag ctt agg gat aat gca aag gag ctg ggt aac ggt tgt ttc      1440
Arg Leu Gln Leu Arg Asp Asn Ala Lys Glu Leu Gly Asn Gly Cys Phe
465                 470                 475                 480 gag ttc tat cat aaa tgt gat aat gaa tgt atg gaa agt gta aga aat      1488
Glu Phe Tyr His Lys Cys Asp Asn Glu Cys Met Glu Ser Val Arg Asn
                485                 490                 495 gga acg tat gac tac ccg cag tat tca gaa gaa gcg aga cta aaa aga      1536
Gly Thr Tyr Asp Tyr Pro Gln Tyr Ser Glu Glu Ala Arg Leu Lys Arg
            500                 505                 510 gag gaa ata agt gga gta aaa ttg gaa tca ata gga att tac caa ata      1584
Glu Glu Ile Ser Gly Val Lys Leu Glu Ser Ile Gly Ile Tyr Gln Ile
        515                 520                 525 ctg tca att tat tct aca gtg gcg agt tcc ctg gca ctg gca atc atg      1632
Leu Ser Ile Tyr Ser Thr Val Ala Ser Ser Leu Ala Leu Ala Ile Met
530                 535                 540 gta gct ggt cta tcc tta tgg atg tgc tcc aat gga tcg tta caa tgc      1680
Val Ala Gly Leu Ser Leu Trp Met Cys Ser Asn Gly Ser Leu Gln Cys
545                 550                 555                 560 aga att tgc att taa                                                   1695
Arg Ile Cys Ile <210> SEQ ID NO 6
<211> LENGTH: 564
<212> TYPE: PRT
<213> ORGANISM: Influenza A virus

<400> SEQUENCE: 6

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Asn Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190
```

```
Gly Ile His His Pro Asn Asp Ala Glu Gln Thr Lys Leu Tyr Gln
        195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
        370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
        450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
        530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 7
<211> LENGTH: 1704
<212> TYPE: DNA
<213> ORGANISM: Influenza A virus
<220> FEATURE:
<221> NAME/KEY: CDS
<222> LOCATION: (1)..(1704)
```

<400> SEQUENCE: 7

```
atg gag aaa ata gtg ctt ctt ctt gca ata gtc agc ctt gtt aaa agt         48
Met Glu Lys Ile Val Leu Leu Leu Ala Ile Val Ser Leu Val Lys Ser
1               5                   10                  15 gat cag att tgc att ggt tac cat gca aac aac tcg aca gag cag gtt         96
Asp Gln Ile Cys Ile Gly Tyr His Ala Asn Asn Ser Thr Glu Gln Val
            20                  25                  30 gac aca ata atg gaa aag aac gtt act gtt aca cat gcc caa gac ata        144
Asp Thr Ile Met Glu Lys Asn Val Thr Val Thr His Ala Gln Asp Ile
        35                  40                  45 ctg gaa aag aca cac aac ggg aag ctc tgc gat cta gat gga gtg aag        192
Leu Glu Lys Thr His Asn Gly Lys Leu Cys Asp Leu Asp Gly Val Lys
    50                  55                  60 cct ctg att tta aga gat tgt agt gta gct gga tgg ctc ctc gga aac        240
Pro Leu Ile Leu Arg Asp Cys Ser Val Ala Gly Trp Leu Leu Gly Asn
65                  70                  75                  80 cca atg tgt gac gaa ttc atc aat gtg ccg gaa tgg tct tac ata gtg        288
Pro Met Cys Asp Glu Phe Ile Asn Val Pro Glu Trp Ser Tyr Ile Val
                85                  90                  95 gag aag gcc aac cca gcc aat gac ctc tgt tac cca ggg aat ttc aac        336
Glu Lys Ala Asn Pro Ala Asn Asp Leu Cys Tyr Pro Gly Asn Phe Asn
            100                 105                 110 gac tat gaa gaa ctg aaa cac cta ttg agc aga ata aac cat ttt gag        384
Asp Tyr Glu Glu Leu Lys His Leu Leu Ser Arg Ile Asn His Phe Glu
        115                 120                 125 aaa att cag atc atc ccc aaa agt tct tgg tcc gat cat gaa gcc tca        432
Lys Ile Gln Ile Ile Pro Lys Ser Ser Trp Ser Asp His Glu Ala Ser
    130                 135                 140 tca ggg gtg agc tca gca tgt cca tac cag gga acg ccc tcc ttt ttc        480
Ser Gly Val Ser Ser Ala Cys Pro Tyr Gln Gly Thr Pro Ser Phe Phe
145                 150                 155                 160 aga aat gtg gta tgg ctt atc aaa aag aac aat aca tac cca aca ata        528
Arg Asn Val Val Trp Leu Ile Lys Lys Asn Asn Thr Tyr Pro Thr Ile
                165                 170                 175 aag aga agc tac aat aat acc aac cag gaa gat ctt ttg ata ctg tgg        576
Lys Arg Ser Tyr Asn Asn Thr Asn Gln Glu Asp Leu Leu Ile Leu Trp
            180                 185                 190 ggg att cat cat tct aat gat gcg gca gag cag aca aag ctc tat caa        624
Gly Ile His His Ser Asn Asp Ala Ala Glu Gln Thr Lys Leu Tyr Gln
        195                 200                 205 aac cca acc acc tat att tcc gtt ggg aca tca aca cta aac cag aga        672
Asn Pro Thr Thr Tyr Ile Ser Val Gly Thr Ser Thr Leu Asn Gln Arg
    210                 215                 220 ttg gta cca aaa ata gct act aga tcc aaa gta aac ggg caa agt gga        720
Leu Val Pro Lys Ile Ala Thr Arg Ser Lys Val Asn Gly Gln Ser Gly
225                 230                 235                 240 agg atg gat ttc ttc tgg aca att tta aaa ccg aat gat gca atc aac        768
Arg Met Asp Phe Phe Trp Thr Ile Leu Lys Pro Asn Asp Ala Ile Asn
                245                 250                 255 ttc gag agt aat gga aat ttc att gct cca gaa tat gca tac aaa att        816
Phe Glu Ser Asn Gly Asn Phe Ile Ala Pro Glu Tyr Ala Tyr Lys Ile
            260                 265                 270 gtc aag aaa ggg gac tca gca att gtt aaa agt gaa gtg gaa tat ggt        864
Val Lys Lys Gly Asp Ser Ala Ile Val Lys Ser Glu Val Glu Tyr Gly
        275                 280                 285 aac tgc aac aca aag tgt caa act cca ata ggg gcg ata aac tct agt        912
Asn Cys Asn Thr Lys Cys Gln Thr Pro Ile Gly Ala Ile Asn Ser Ser
    290                 295                 300
```

| | | | | | | | | | | | | | | | | |
|---|---|---|---|---|---|---|---|---|---|---|---|---|---|---|---|---|
| atg | cca | ttc | cac | aac | ata | cac | cct | ctc | acc | atc | ggg | gaa | tgc | ccc | aaa | 960 |
| Met | Pro | Phe | His | Asn | Ile | His | Pro | Leu | Thr | Ile | Gly | Glu | Cys | Pro | Lys | |
| 305 | | | | 310 | | | | | 315 | | | | | 320 | | |
| tat | gtg | aaa | tca | aac | aaa | tta | gtc | ctt | gcg | act | ggg | ctc | aga | aat | agt | 1008 |
| Tyr | Val | Lys | Ser | Asn | Lys | Leu | Val | Leu | Ala | Thr | Gly | Leu | Arg | Asn | Ser | |
| | | | | 325 | | | | | 330 | | | | | 335 | | |
| cct | cta | aga | gaa | aga | aga | aaa | aga | gga | cta | ttt | gga | gct | ata | gca | 1056 | |
| Pro | Leu | Arg | Glu | Arg | Arg | Lys | Arg | Gly | Leu | Phe | Gly | Ala | Ile | Ala | | |
| | | | 340 | | | | | 345 | | | | | 350 | | | |
| ggg | ttt | ata | gag | gga | gga | tgg | cag | gga | atg | gta | gat | ggt | tgg | tat | ggg | 1104 |
| Gly | Phe | Ile | Glu | Gly | Gly | Trp | Gln | Gly | Met | Val | Asp | Gly | Trp | Tyr | Gly | |
| | | 355 | | | | | 360 | | | | | 365 | | | | |
| tac | cac | cat | agc | aat | gag | cag | ggg | agt | ggg | tac | gct | gca | gac | aaa | gaa | 1152 |
| Tyr | His | His | Ser | Asn | Glu | Gln | Gly | Ser | Gly | Tyr | Ala | Ala | Asp | Lys | Glu | |
| | 370 | | | | | 375 | | | | | 380 | | | | | |
| tcc | act | caa | aag | gca | ata | gat | gga | gtc | acc | aat | aag | gtc | aac | tcg | atc | 1200 |
| Ser | Thr | Gln | Lys | Ala | Ile | Asp | Gly | Val | Thr | Asn | Lys | Val | Asn | Ser | Ile | |
| 385 | | | | | 390 | | | | | 395 | | | | | 400 | |
| att | gac | aaa | atg | aac | act | cag | ttt | gag | gcc | gtt | gga | agg | gaa | ttt | aat | 1248 |
| Ile | Asp | Lys | Met | Asn | Thr | Gln | Phe | Glu | Ala | Val | Gly | Arg | Glu | Phe | Asn | |
| | | | | 405 | | | | | 410 | | | | | 415 | | |
| aac | tta | gaa | agg | aga | ata | gag | aat | tta | aac | aag | aaa | atg | gaa | gac | gga | 1296 |
| Asn | Leu | Glu | Arg | Arg | Ile | Glu | Asn | Leu | Asn | Lys | Lys | Met | Glu | Asp | Gly | |
| | | | 420 | | | | | 425 | | | | | 430 | | | |
| ttc | cta | gat | gtc | tgg | act | tat | aat | gct | gaa | ctt | ctg | gtt | ctc | atg | gaa | 1344 |
| Phe | Leu | Asp | Val | Trp | Thr | Tyr | Asn | Ala | Glu | Leu | Leu | Val | Leu | Met | Glu | |
| | | 435 | | | | | 440 | | | | | 445 | | | | |
| aat | gag | aga | act | cta | gac | ttc | cat | gat | tca | aat | gtc | aag | aac | ctt | tac | 1392 |
| Asn | Glu | Arg | Thr | Leu | Asp | Phe | His | Asp | Ser | Asn | Val | Lys | Asn | Leu | Tyr | |
| | 450 | | | | | 455 | | | | | 460 | | | | | |
| gac | aag | gtc | cga | cta | cag | ctt | agg | gat | aat | gca | aag | gag | ctg | ggt | aac | 1440 |
| Asp | Lys | Val | Arg | Leu | Gln | Leu | Arg | Asp | Asn | Ala | Lys | Glu | Leu | Gly | Asn | |
| 465 | | | | 470 | | | | | 475 | | | | | 480 | | |
| ggt | tgt | ttc | gag | ttc | tat | cac | aaa | tgt | gat | aat | gaa | tgt | atg | gaa | agt | 1488 |
| Gly | Cys | Phe | Glu | Phe | Tyr | His | Lys | Cys | Asp | Asn | Glu | Cys | Met | Glu | Ser | |
| | | | 485 | | | | | 490 | | | | | 495 | | | |
| gta | aga | aac | gga | acg | tat | gac | tac | ccg | cag | tat | tca | gaa | gaa | gca | aga | 1536 |
| Val | Arg | Asn | Gly | Thr | Tyr | Asp | Tyr | Pro | Gln | Tyr | Ser | Glu | Glu | Ala | Arg | |
| | | 500 | | | | | 505 | | | | | 510 | | | | |
| tta | aaa | aga | gag | gaa | ata | agt | gga | gta | aaa | ttg | gaa | tca | ata | gga | act | 1584 |
| Leu | Lys | Arg | Glu | Glu | Ile | Ser | Gly | Val | Lys | Leu | Glu | Ser | Ile | Gly | Thr | |
| | 515 | | | | | 520 | | | | | 525 | | | | | |
| tac | caa | ata | ctg | tca | att | tat | tca | aca | gtt | gcg | agt | tct | cta | gca | ctg | 1632 |
| Tyr | Gln | Ile | Leu | Ser | Ile | Tyr | Ser | Thr | Val | Ala | Ser | Ser | Leu | Ala | Leu | |
| 530 | | | | | 535 | | | | | 540 | | | | | | |
| gca | atc | atg | gtg | gct | ggt | cta | tct | ttg | tgg | atg | tgc | tcc | aat | ggg | tcg | 1680 |
| Ala | Ile | Met | Val | Ala | Gly | Leu | Ser | Leu | Trp | Met | Cys | Ser | Asn | Gly | Ser | |
| 545 | | | | 550 | | | | | 555 | | | | | 560 | | |
| tta | caa | tgc | aga | att | tgc | att | taa | | | | | | | | | 1704 |
| Leu | Gln | Cys | Arg | Ile | Cys | Ile | | | | | | | | | | |
| | | | 565 | | | | | | | | | | | | | |

<210> SEQ ID NO 8
<211> LENGTH: 567
<212> TYPE: PRT
<213> ORGANISM: Influenza A virus

<400> SEQUENCE: 8

Met Glu Lys Ile Val Leu Leu Leu Ala Ile Val Ser Leu Val Lys Ser
1               5                   10                  15

-continued

```
Asp Gln Ile Cys Ile Gly Tyr His Ala Asn Asn Ser Thr Glu Gln Val
                20                  25                  30
Asp Thr Ile Met Glu Lys Asn Val Thr Val Thr His Ala Gln Asp Ile
            35                  40                  45
Leu Glu Lys Thr His Asn Gly Lys Leu Cys Asp Leu Asp Gly Val Lys
        50                  55                  60
Pro Leu Ile Leu Arg Asp Cys Ser Val Ala Gly Trp Leu Leu Gly Asn
65                  70                  75                  80
Pro Met Cys Asp Glu Phe Ile Asn Val Pro Glu Trp Ser Tyr Ile Val
                85                  90                  95
Glu Lys Ala Asn Pro Ala Asn Asp Leu Cys Tyr Pro Gly Asn Phe Asn
            100                 105                 110
Asp Tyr Glu Glu Leu Lys His Leu Leu Ser Arg Ile Asn His Phe Glu
        115                 120                 125
Lys Ile Gln Ile Ile Pro Lys Ser Ser Trp Ser Asp His Glu Ala Ser
    130                 135                 140
Ser Gly Val Ser Ser Ala Cys Pro Tyr Gln Gly Thr Pro Ser Phe Phe
145                 150                 155                 160
Arg Asn Val Val Trp Leu Ile Lys Lys Asn Asn Thr Tyr Pro Thr Ile
                165                 170                 175
Lys Arg Ser Tyr Asn Asn Thr Asn Gln Glu Asp Leu Leu Ile Leu Trp
            180                 185                 190
Gly Ile His His Ser Asn Asp Ala Ala Glu Gln Thr Lys Leu Tyr Gln
        195                 200                 205
Asn Pro Thr Thr Tyr Ile Ser Val Gly Thr Ser Thr Leu Asn Gln Arg
    210                 215                 220
Leu Val Pro Lys Ile Ala Thr Arg Ser Lys Val Asn Gly Gln Ser Gly
225                 230                 235                 240
Arg Met Asp Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Ala Ile Val Lys Ser Glu Val Glu Tyr Gly
        275                 280                 285
Asn Cys Asn Thr Lys Cys Gln Thr Pro Ile Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Lys Leu Val Leu Ala Thr Gly Leu Arg Asn Ser
                325                 330                 335
Pro Leu Arg Glu Arg Arg Arg Lys Arg Gly Leu Phe Gly Ala Ile Ala
            340                 345                 350
Gly Phe Ile Glu Gly Gly Trp Gln Gly Met Val Asp Gly Trp Tyr Gly
        355                 360                 365
Tyr His His Ser Asn Glu Gln Gly Ser Gly Tyr Ala Ala Asp Lys Glu
    370                 375                 380
Ser Thr Gln Lys Ala Ile Asp Gly Val Thr Asn Lys Val Asn Ser Ile
385                 390                 395                 400
Ile Asp Lys Met Asn Thr Gln Phe Glu Ala Val Gly Arg Glu Phe Asn
                405                 410                 415
Asn Leu Glu Arg Arg Ile Glu Asn Leu Asn Lys Lys Met Glu Asp Gly
            420                 425                 430
Phe Leu Asp Val Trp Thr Tyr Asn Ala Glu Leu Leu Val Leu Met Glu
```

```
                 435                 440                 445
Asn Glu Arg Thr Leu Asp Phe His Asp Ser Asn Val Lys Asn Leu Tyr
        450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 9
<211> LENGTH: 552
<212> TYPE: PRT
<213> ORGANISM: Influenza A virus

<400> SEQUENCE: 9

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Ala Ile Leu Lys Pro Asn Asp Ala Ile Asn
225                 230                 235                 240
```

-continued

```
Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
        515                 520                 525

Leu Ala Ile Met Ile Ala Gly Leu Ser Leu Trp Met Cys Ser Asn Gly
    530                 535                 540

Ser Leu Gln Cys Arg Ile Cys Ile
545                 550

<210> SEQ ID NO 10
<211> LENGTH: 548
<212> TYPE: PRT
<213> ORGANISM: Influenza A virus

<400> SEQUENCE: 10

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60
```

```
Pro Met Cys Asp Glu Phe Ile Asn Val Pro Glu Trp Ser Tyr Ile Val
 65                  70                  75                  80

Glu Lys Ala Asn Pro Val Asn Asp Leu Cys Tyr Pro Gly Asp Phe Asn
                 85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Asn Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480
```

```
Gly Thr Tyr Asp Tyr Pro Gln Tyr Ser Glu Ala Arg Leu Lys Arg
                485                 490                 495

Glu Glu Ile Ser Gly Val Lys Leu Glu Ser Ile Gly Ile Tyr Gln Ile
            500                 505                 510

Leu Ser Ile Tyr Ser Thr Val Ala Ser Ser Leu Ala Leu Ala Ile Met
            515                 520                 525

Val Ala Gly Leu Ser Leu Trp Met Cys Ser Asn Gly Ser Leu Gln Cys
530                 535                 540

Arg Ile Cys Ile
545

<210> SEQ ID NO 11
<211> LENGTH: 551
<212> TYPE: PRT
<213> ORGANISM: Influenza A virus

<400> SEQUENCE: 11

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Thr Pro Ser Phe Phe
130                 135                 140

Arg Asn Val Val Trp Leu Ile Lys Lys Asn Asn Thr Tyr Pro Thr Ile
145                 150                 155                 160

Lys Arg Ser Tyr Asn Asn Thr Asn Gln Glu Asp Leu Leu Ile Leu Trp
                165                 170                 175

Gly Ile His His Ser Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Val Lys Ser Glu Val Glu Tyr Gly
            260                 265                 270

Asn Cys Asn Thr Lys Cys Gln Thr Pro Ile Gly Ala Ile Asn Ser Ser
        275                 280                 285

Met Pro Phe His Asn Ile His Pro Leu Thr Ile Gly Glu Cys Pro Lys
290                 295                 300
```

-continued

```
Tyr Val Lys Ser Asn Lys Leu Val Leu Ala Thr Gly Leu Arg Asn Ser
305                 310                 315                 320

Pro Leu Arg Glu Arg Arg Lys Arg Gly Leu Phe Gly Ala Ile Ala
            325                 330                 335

Gly Phe Ile Glu Gly Gly Trp Gln Gly Met Val Asp Gly Trp Tyr Gly
            340                 345                 350

Tyr His His Ser Asn Glu Gln Gly Ser Gly Tyr Ala Ala Asp Lys Glu
        355                 360                 365

Ser Thr Gln Lys Ala Ile Asp Gly Val Thr Asn Lys Val Asn Ser Ile
    370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
            405                 410                 415

Phe Leu Asp Val Trp Thr Tyr Asn Ala Glu Leu Leu Val Leu Met Glu
            420                 425                 430

Asn Glu Arg Thr Leu Asp Phe His Asp Ser Asn Val Lys Asn Leu Tyr
        435                 440                 445

Asp Lys Val Arg Leu Gln Leu Arg Asp Asn Ala Lys Glu Leu Gly Asn
    450                 455                 460

Gly Cys Phe Glu Phe Tyr His Lys Cys Asp Asn Glu Cys Met Glu Ser
465                 470                 475                 480

Val Arg Asn Gly Thr Tyr Asp Tyr Pro Gln Tyr Ser Glu Glu Ala Arg
            485                 490                 495

Leu Lys Arg Glu Glu Ile Ser Gly Val Lys Leu Glu Ser Ile Gly Thr
            500                 505                 510

Tyr Gln Ile Leu Ser Ile Tyr Ser Thr Val Ala Ser Ser Leu Ala Leu
        515                 520                 525

Ala Ile Met Val Ala Gly Leu Ser Leu Trp Met Cys Ser Asn Gly Ser
    530                 535                 540

Leu Gln Cys Arg Ile Cys Ile
545                 550
```

UNIVERSAL VACCINE AGAINST H5N1 LINEAGES

CROSS-REFERENCE TO RELATED APPLICATIONS

The present application is a 35 U.S.C. §371 National Phase Entry Application of PCT/SG2011/000059, filed 9 Feb. 2011, and designating the United States, which in turn is related to and claims priority to U.S. provisional patent application Ser. No. 61/329,802, filed 30 Apr. 2010, each application is incorporated herein by reference.

SEQUENCE SUBMISSION

The present application is being filed along with a Sequence Listing in electronic format. The Sequence Listing is entitled 2577-201PCT_ST25.txt, was created on 13 Jan. 2011 and is 54 kb in size. The information in the electronic format of the Sequence Listing is part of the present application and is incorporated herein by reference in its entirety.

BACKGROUND OF THE INVENTION

The present invention relates to a universal H5N1 vaccine. More specifically, the present invention relates to the identification of three H5N1 strains which cover the entire variants in the neutralizing epitopes of hemagglutinin among most H5N1 lineages. The present invention further relates a universal H5N1 vaccine that comprises the three H5N1 strains or that comprises hemagglutinin peptides of each of these three strains.

The publications and other materials used herein to illuminate the background of the invention or provide additional details respecting the practice, are incorporated by reference, and for convenience are respectively grouped in the Bibliography.

Influenza virus evades immune system by randomly changing the antigenic determinants, such as the major neutralizing epitopes, present in the globular head region of hemagglutinin. Upon infection, host response is mainly characterized by the induction of antibodies against such neutralizing epitopes, which blocks the attachment of viral hemagglutinin to the target cell receptor. However, considerable amino acid variations within these neutralizing epitopes of HA lead to the emergence of antigenically distinct influenza H5N1 viruses. In fact, it has been reported that seasonal influenza viruses were able to efficiently escape from vaccine-induced immunity in human population through antigenic drift. Moreover, mutation of a few key amino acids in HA1 variable regions is sufficient to allow viral escape from vaccine-induced antibody responses. Previous attempts to identify the amino acid substitutions within HA sequences of variants escaped from neutralization by monoclonal antibodies has revealed neutralizing epitope sites of HA (Kaverin et al., 2002; Kaverin et al., 2007).

The nature of influenza virus to randomly mutate and evolve into new types with diverse antigenic determinants is an important challenge in the control of influenza infection (Plotkin et al., 2002). This has been evidently recognized by the recent outbreaks of H5N1 avian flu and the current pandemic situation with H1N1 swine-origin influenza A virus (S-OIV). In fact, it has been well documented in literature that H5N1 had acquired the ability to infect human tissues due mainly to the occurrence of mutation events (Ayora-Talayera et al., 2009). Highly pathogenic avian influenza (HPAI) H5N1 are antigenically distinguishable owing to the differences in the hemagglutinin (HA) sequences, the principal determinant of immunity to influenza, resulting in different lineages or clades of H5N1 (Lam et al., 2008; WHO, 2005). Control of infection with current H5N1 vaccines does not appear to be effective against heterologous strains or phylogenetically variant clades of H5N1 in part due to the variation in the HA sequences, particularly within the neutralizing epitope region. Since present vaccines are solely based on the induction of neutralizing antibodies against these epitopes, differences in these sequences may render the current vaccines unqualified for prevention of influenza globally. In fact, current H5N1 vaccine candidates continue to provide good antigenic coverage of most isolates within corresponding clades, it has been recently recognized that some viruses within clades 1, 2.2 and 2.3 itself shows evidence of antigenic heterogeneity.

To overcome such limitations and to completely realize the potential of vaccines worldwide, the concept of universal vaccines based on conserved viral proteins has been recently proposed. Highly conserved ion channel protein (M2) or the nucleoprotein (NP) of influenza virus has been evaluated for the induction of cross-protective cellular immunity and viral clearance (Wu et al., 2007; Chen and Subbarao, 2009). A similar approach with conserved fusion peptide of the hemagglutinin is another option to inhibit the fusion of the virus to the host cell membrane (Gerhard et al., 2006). Antibodies generated against these conserved proteins may reduce viral spread and accelerate recovery from influenza. However, antibodies specific to these proteins are poorly immunogenic and found to be infection permissive. Thus, development of vaccine based on the influenza virus hemagglutinin appears to be the only viable option to prevent infections by HPAI such as H5N1. Nevertheless, amino acid variations within the major antigenic neutralizing epitope region among the H5 subtype restricts the development of such universal vaccines against different H5N1 lineages.

Therefore, it is desired to develop a universal vaccine that provides some degree of protective immunity against different H5N1 lineages.

SUMMARY OF THE INVENTION

The present invention relates to a universal H5N1 vaccine. More specifically, the present invention relates to the identification of three H5N1 strains which cover the entire variants in the neutralizing epitopes of hemagglutinin among most H5N1 lineages. The present invention further relates a universal H5N1 vaccine that comprises the three H5N1 strains or that comprises hemagglutinin peptides of each of these three strains.

Thus, in a first aspect, the present invention provides a universal H5N1 vaccine for the prevention of a disease in a subject, wherein the disease is associated with an H5N1 subtype of avian influenza virus. In one embodiment, the universal H5N1 vaccine comprises a prophylactically effective amount of a first immunogenic agent, a prophylactically effective amount of a second immunogenic agent and a prophylactically effective amount of a third immunogenic agent. In another embodiment, each immunogenic agent comprises a hemagglutinin or antigenic portion thereof or a nucleic acid encoding the hemagglutinin or antigenic portion thereof. In an additional embodiment, the antigenic portion includes an epitope of hemagglutinin. In a further embodiment, the subjects may be humans, domestic animals (dog, cat, monkey etc.); livestock (horse, cow, sheep, goat, pig etc.), wild birds (wild geese, wild ducks, etc.) and domestic birds (chicken, duck, geese etc.). In one embodiment, an immunogenic agent is virus comprising hemagglutinin. In another embodiment, the virus is inactivated. In an additional embodiment, the virus is an attenuated virus. In another embodiment, the virus is in the form of a virosome. In a further embodiment, the virus is egg-derived or cell culture-derived. In another embodiment, the immunogenic agent is a split virus comprising hemagglutinin or a split virus antigenic preparation. In one embodiment, the immunogenic agent is hemagglutinin or antigenic portion thereof. In another embodiment, the hemagglutinin or antigenic portion thereof has been isolated. In an additional embodiment, the hemagglutinin or antigenic portion thereof is produced by an expression system. In one embodiment, the expression system is any expression system, such as a viral expression vector in which the hemagglutinin or antigenic portion thereof is presented or displayed on the surface of the virus. In one embodiment, the viral expression vector is any viral expression vector such as a modified vaccinia virus expression vector, an adenovirus expression vector, a poxvirus expression vector, a baculovirus expression vector and the like. In one embodiment, the expression vector is a baculovirus expression vector and the virus presenting or displaying the hemagglutinin or antigenic portion thereof is a baculovirus. In another embodiment, the immunogenic agent is a nucleic acid encoding the hemagglutinin or antigenic portion thereof which is capable of expression in the subject.

In a second aspect, the present invention provides a method for producing protective immunity to an avian influenza virus which comprises administering to a subject a prophylactically effective amount of a universal H5N1 vaccine. The universal H5N1 vaccine is as described above.

In a third aspect, the present invention provides a method for the prevention or treatment of a disease associated with an avian influenza virus which comprises administering to a subject a prophylactically effective amount of a universal H5N1 vaccine. The universal H5N1 vaccine is as described above.

In a fourth aspect, the present invention provides use of a universal H5N1 vaccine for stimulating an immune response to an avian influenza virus. The universal H5N1 vaccine is as described above.

In a fifth aspect, the present invention provides use of a universal H5N1 vaccine for the prevention of a disease associated with an avian influenza virus. The universal H5N1 vaccine is as described above.

In a sixth aspect, the present invention provides a universal H5N1 vaccine for use in medicine.

In a seventh aspect, the present invention provides a universal H5N1 vaccine for use in modulating an immune response in a subject.

In an eighth aspect, the present invention provides a universal H5N1 vaccine for use in treating or preventing a disease associated with an avian influenza virus in a subject.

In a ninth aspect, the present invention provides use of a universal H5N1 vaccine for the manufacture of a medicament for modulating an immune response in a subject.

In a tenth aspect, the present invention provides use of a universal H5N1 vaccine for the manufacture of a medicament for treating or preventing a disease associated with an avian influenza virus in a subject.

BRIEF DESCRIPTION OF THE FIGURES

FIGS. 2A and 2B show cross clade serum microneutralization in mice. Groups of mice were subcutaneously immunized two times on days 0 and 28 with three strains of BacHA (Tri-BacHA) or single strain (A/Vietnam/1203/2004 (H5N1)) of BacHA (Mono-BacHA) or inactivated whole H5N1 viral vaccine (WT-H5N1). The viruses from clade 1.0 (A/Vietnam/1203/2004(H5N1)), clade 2.1 (A/Indonesia/CDC1031/2007(H5N1)), clade 2.2 A/turkey/Turkey1/05* (H5N1), clade 4.0 (clade 4.0 A/goose/Guiyang/337/06 (H5N1)), clade 7.0 (A/chicken/Shanxi/2/06(H5N1)) and clade 8.0 (A/chicken/Henan/12/04(H5N1)) were used for this study. Clades 1, 2.1 and 2.2 are shown in FIG. 2A, and clades 4, 7 and 8 are shown in FIG. 2B. The sera from the day of peak response, day 14 after the final immunization, were used for the assay. Each point represents the arithmetic mean value (n=10)±SE.

FIG. 3 show protection of mice from lethal H5N1 viral challenge. Groups of mice were subcutaneously immunized two times on days 0 and 28 with three strains of BacHA (Tri-BacHA) or single strain (A/Vietnam/1203/2004 (H5N1)) of BacHA (Mono-BacHA) or inactivated whole H5N1 viral vaccine (WT-H5N1). Three weeks after the final vaccination, mice were intranasally infected with 5MLD50 (Mouse lethal dose 50%) of clade 1.0 (A/Vietnam/1203/2004(H5N1)) HPAI H5N1 strains. Mice were monitored for survival throughout a 14 day observation period. The results are expressed in terms of percent survival.

FIG. 5 shows protection of mice from lethal H5N1 viral challenge. Groups of mice were subcutaneously immunized two times on days 0 and 28 with three strains of BacHA (Tri-BacHA) or single strain (A/Vietnam/1203/2004 (H5N1)) of BacHA (Mono-BacHA) or inactivated whole H5N1 viral vaccine (WT-H5N1). Three weeks after the final vaccination, mice were intranasally infected with 5MLD50 (Mouse lethal dose 50%) of clade 7.0 (A/chicken/Shanxi/2/06(H5N1)) HPAI H5N1 strain. Mice were monitored for weight loss throughout a 14 day observation period. The results are expressed in terms of percent body weight (at the beginning of the trial).

FIG. 6 shows protection of mice from lethal H5N1 viral challenge. Groups of mice were subcutaneously immunized two times on days 0 and 28 with three strains of BacHA (Tri-BacHA) or single strain (A/Vietnam/1203/2004 (H5N1)) of BacHA (Mono-BacHA) or inactivated whole H5N1 viral vaccine (WT-H5N1). Three weeks after the final vaccination, mice were intranasally infected with 5MLD50 (Mouse lethal dose 50%) of clade 7.0 (A/chicken/Shanxi/2/06(H5N1)) HPAI H5N1 strain. The mice were monitored for survival throughout a 14 day observation period. The results are expressed in terms of percent survival.

DETAILED DESCRIPTION OF THE INVENTION

Figure 1:
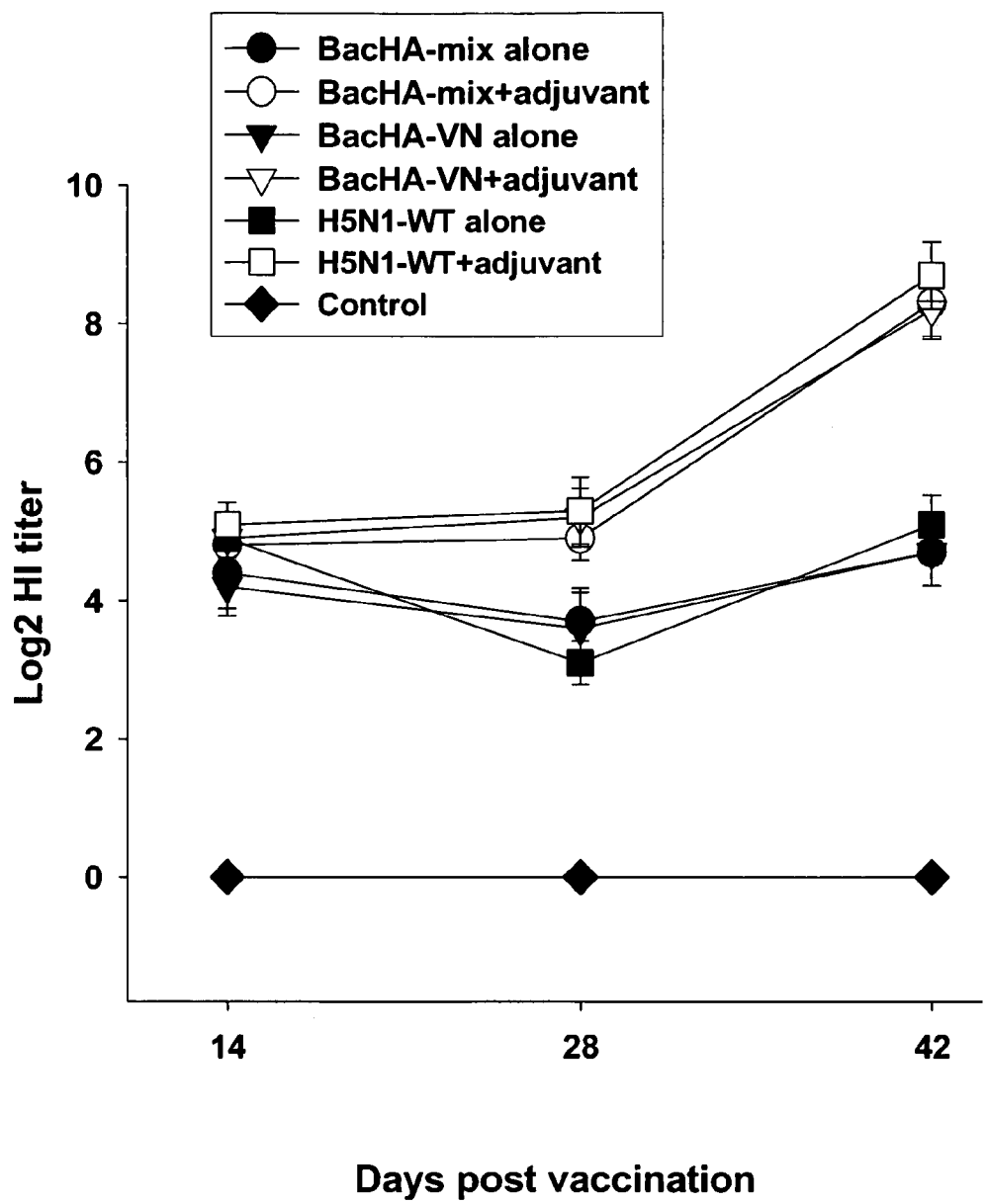
FIG. 1 shows a serum hemagglutination inhibition titer. Groups of mice were subcutaneously immunized two times on days 0 and 28 with Tri-BacHA (BacHA-mix) or Mono-BacHA (A/Vietnam/1203/2004(H5N1)) of BacHA (BacHA-VN) or inactivated whole viral vaccine (WT-H5N1). Each point represents the arithmetic mean value (n=10)±SD.

The present invention relates to a universal H5N1 vaccine. More specifically, the present invention relates to the identification of three H5N1 strains which cover the entire variants in the neutralizing epitopes of hemagglutinin among most H5N1 lineages. The present invention further relates a universal H5N1 vaccine that comprises the three H5N1 strains or that comprises hemagglutinin peptides of each of these three strains.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety for all that they disclose.

Though, current H5N1 vaccine candidates continue to provide good antigenic coverage of most isolates within corresponding clades, it has been recently recognized that some viruses within clades 1, 2.2 and 2.3 itself shows evidence of antigenic heterogeneity. Since H5N1 viruses have already split into numerous sublineages or clades, the present invention provides an analysis and selection of vaccine strains that represents the variations among H5 subtypes particularly in the region of neutralizing epitopes. Such vaccine strain selection in accordance with the present invention provides a broad range of protection against most H5N1 lineages.

As shown herein, development of universal vaccine entirely based on HA of influenza virus is feasible, if the variation or conservation of neutralizing epitopes among the several HPAI H5N1 clades can be identified. Understanding the distribution pattern of such neutralizing epitopes helped in the design of a universal vaccine by incorporating two or more ideal H5N1 strains in the vaccine composition. The neutralizing epitopes of the selected viral strains cover the variations among the most H5 subtypes, in order to acquire broad range protective immunity against most H5N1 subtypes. Previous attempts to identify the amino acid substitutions within HA sequences of variants escaped from neutralization by monoclonal antibodies revealed the neutralizing epitope sites of HA (Kaverin et al., 2002; Kaverin et al., 2007). Along with previous findings, the present invention provides the identification of other major neutralizing epitopes of H5N1 by mapping their amino acid sequences using neutralizing monoclonal antibodies. Analysis of distribution of all identified neutralizing epitopes among H5 subtypes revealed the variations within the antigenic determinants of H5N1 subtypes from both human and avian resources. Based on these results, the present invention provides three vaccine strains comprising the major neutralizing epitopes of HA to cover the entire variants within the H5N1 lineages. In order to test demonstrate the broad range of protection in vivo, HA proteins of selected vaccine strains were expressed on the baculovirus surface and the efficacy of the vaccine formulations were evaluated in a mouse model challenged with phylogenetically variant H5N1 strains.

In accordance with the present invention, the universal vaccine development strategy involved three steps: (i) mapping of neutralizing epitopes of H5N1 virus hemagglutinin using neutralizing monoclonal antibodies (n-mAbs); (ii) analyzing the distribution of neutralizing epitopes among all H5N1 lineages; and (iii) selecting ideal vaccine strains to cover the variations within the neutralizing epitopes of entire H5N1 viruses. In accordance with the present invention, a panel of five n-mAbs (6B8, 4C2, 2D9, 4F8 and 3H11) was used to map the neutralizing epitopes of H5N1 virus. Mapping of neutralizing epitopes with n-mAbs revealed that amino acids at position 138 or 155 or 189 or 223 were involved in the formation of major neutralizing epitopes of H5N1 virus hemagglutinin. In addition, other amino acids (140, 159, 194 and 218) identified as part of the major neutralizing epitopes (Kaverin et al., 2007) were also taken into consideration for subsequent analysis. As shown herein, comparison of major neutralizing epitope sequences of H5N1 viruses with influenza research database revealed the variations within the epitope region of all human and avian H5N1 virus hemagglutinin. See Table 2, below.

Based on the epitope distribution analysis described herein, three different strains, A/Indonesia/CDC669/2006 (H5N1) (clade 2.1), A/Viet Nam/1203/2004(H5N1) (clade 1.0) and Anhui/1/2005(H5N1) (clade 2.3) were selected to collectively represent the variations among all H5N1 subtypes. The selected vaccine strains were confirmed for the reactivity pattern with different neutralizing mAbs by virus neutralization and HI titers. As shown in Tables 4A and 4B, below, n-mAb 4C2 and 4F8 recognizes only the A/Indonesia/CDC669/2006(H5N1) strain and did not react with the A/Vietnam/1203/2004(H5N1) and A/Anhui/1/2005(H5N1) strains. This pattern of reactivity could be possibly due to the change in the amino acid at position 189 as the A/Indonesia/CDC669/2006(H5N1) strain has "Arg" at position 189 while "Lys" is present in the A/Vietnam/1203/2004(H5N1) and A/Anhui/1/2005(H5N1) strains at the same position. On the other hand, n-mAb 6B8 reacts with both the A/Vietnam/1203/2004(H5N1) and A/Anhui/1/2005(H5N1) strains possibly due to the presence of common residue "Lys" at position at 189. Similarly, amino acid at position 155 has also been found to have a significant impact on the antibody recognition of H5N1 strains. Moreover, as shown in Table 2, below, 150's loop has two variants with 63.4% of human H5N1 isolates have amino acid "Ser" and remaining 34.4% have amino acid "Asn" at this position. Also, amino acid at position 189, located in the receptor binding site of HA, contains amino acid "Arg" in 64.26% of all H5N1 human strains while remaining 34.65% have amino acid "Lys" at this position. Hence, it is reasonable to speculate that the vaccine strains selected in accordance with the present invention should represent the variations within the major antigenic epitopes of almost 99% of all H5N1 lineages including both human and avian viruses.

HA proteins of selected strains were individually expressed on the baculovirus surface and the vaccine formulation was evaluated in a mouse model. A recombinant baculovirus with the immediate early promoter 1 (ie1) of WSSV was constructed to facilitate high level expression of influenza H5 hemagglutinin in both insect and mammalian cells. The nature of ie1 as an immediate early promoter supports the protein expression at the early phase of the baculoviral lifecycle, resulting in enhanced display of functional hemagglutinin on the baculovirus envelope. As the oligomerization is required for efficient transport of the HA proteins to the host cell membrane (Copeland et al., 1986), a pre-requisite for the baculovirus to acquire the protein, it is presumed that HA displayed on the baculovirus surface should have been presented in their oligomeric forms. Hence, this model will help mimic the native structure of the protein, thus imitating the wild-type influenza virus. HA displayed on the baculovirus surface has retained its native structure as evidenced by the hemagglutination activity and authentic cleavage of HA0 into HA1 and HA2 (data not shown). Though baculovirus expressed influenza hemagglutinin (HA) are generally not cleaved in insect cells, HA of highly pathogenic avian influenza viruses (such as H5 and H7) with multiple basic amino acids at the cleavage site has been shown to be cleaved into HA1 and HA2 subunits in the absence of trypsin or trypsin-like proteases (Kuroda et al., 1986). The partial cleavage of HA0 in the current study may be possibly due to the presence of subtilisin like proprotein convertases (PC) in insect cells (Cieplik et al., 1998), whose substrate specificity and inhibitor profiles are identical to mammalian PCs.

As shown herein, subcutaneous immunization of an adjuvanted mixture of each baculovirus displaying HA from A/Indonesia/CDC669/2006(H5N1), A/Viet Nam/1203/2004 (H5N1) or A/Anhui/1/2005(H5N1) (Tri-BacHA) significantly enhanced the serum HI titre when compared to its unadjuvanted counterpart. Moreover, HI titer of mice vaccinated with adjuvanted Tri-BacHA was comparable with those (against A/Vietnam/1203/2004(H5N1)) vaccinated with either adjuvanted whole RG-H5N1 virus or adjuvanted baculovirus displaying HA of H5N1-A/VietNam/1203/2004 (H5N1) (Mono-BacHA). In addition, adjuvanted Tri-BacHA induced higher neutralization antibody titers, which efficiently neutralized 100 TCID50 of heterologous H5N1 strains from various clades (clade 1.0, clade 2.1, clade 2.2, clade 4.0, clade 7.0 and clade 8.0) compared to unadjuvanted Tri-BacHA. Vaccine formulations containing only adjuvanted Mono-BacHA or inactivated RG-H5N1 vaccine were able to neutralize clade 1 (homologous), clade 2.1 and clade 8.0 but did not efficiently neutralize H5N1 viruses from other clades (clade 2.2, clade 4.0 and clade 7.0). The strong cross-clade immunity of the adjuvanted Tri-BacHA vaccine formulation could be due to the coverage of variations within the neutralizing epitopes of H5N1 lineages.

The protective efficacy of the vaccine was evaluated by challenging the vaccinated mice with H5N1 strains from clade 1, clade 2.1 and clade 7. As shown herein, one hundred percent survival rate was obtained with the group vaccinated with adjuvanted Tri-BacHA or Mono-BacHA or inactivated whole viral vaccine against clade 1.0 and clade 2.1. In addition, adjuvanted Tri-BacHA provided 100% protection against clade 7.0 H5N1 virus without any infection symptoms. However, adjuvanted inactivated whole viral vaccine and Mono-BacHA provided only 66.6% and 83.3% protection against clade 7.0 H5N1 infection, respectively. Also, the progression of infection was indicated by varying trends of decrease in body weight in the different groups. Mice vaccinated with adjuvanted Mono-BacHA or adjuvanted whole viral vaccine showed a higher loss of body weight of up to 17% on day 6 against clade 7.0. This indicates the inability of monovalent vaccines to confer protection against diverse H5N1 subtypes, which might be due to the variation within the antigenic determinants (such as neutralizing epitopes) of different virus subtypes.

In summary, subcutaneous immunization of mice with baculovirus displaying hemagglutinin from three selected vaccine strains induced systemic immune responses and exhibited cross protection against H5N1 viral infection without any clinical symptoms. Also, the present findings revealed that selection of vaccine strains based on the variations within the neutralizing epitopes among the subtypes will help prevent the infection mediated by newly emerged H5N1 mutants. The vaccine formulation used in this study was produced rapidly without any biosafety concerns. Baculovirus displaying HA will serve as an ideal choice for a vaccine in pandemic and pre-pandemic situation and expedite the vaccine technology without the requirement of high biocontainment facilities or tedious protein purification processes.

As used herein the terms "treating" and "treatment" refer to any and all uses which remedy a condition or symptoms, prevent the establishment of a condition or disease, or otherwise prevent, hinder, retard, ameliorate or reverse the progression of a condition or disease or other undesirable symptoms in any way whatsoever.

As used herein the term "effective amount" or a "prophylactically effective amount" includes within its meaning a non-toxic but sufficient amount of an agent or compound to provide the desired effect. For example, a prophylactically effective amount for modulating an immune response is an amount of the agent or compound that provides the desired effect of modulating the immune response in the subject. Similarly, a prophylactically effective amount for treating or preventing a disease associated with an avian influenza virus is an amount of the agent or compound that provides the desired effect of treating or preventing the disease in the subject. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount." However, for any given case, an appropriate "effective amount" may be determined by one of ordinary skill in the art using only routine experimentation.

As used herein, the terms "polypeptide", "peptide" and "protein" are used interchangeably to refer to a polymer of amino acid residues and to fragments, variants, analogues, orthologs or homologues thereof. Thus, these terms apply both to amino acid polymers in which one or more amino acid residues is a synthetic non-naturally occurring amino acid, such as a chemical analogue of a corresponding naturally occurring amino acid, as well as to naturally-occurring amino acid polymers.

As used herein, the terms "polynucleotide" or "nucleic acid" are used interchangeably and designate a molecule comprising one or more nucleotides, or an oligonucleotide, or a fragment thereof, including but not limited to RNA or DNA nucleotides or combinations thereof.

As used herein, the phrase "disease associated with an H5N1 subtype avian influenza virus" means any disease, disease state or disorder caused by or associated with an H5N1 subtype avian influenza virus.

As used herein, the term "modulating" when used in relation to an immune response means increasing or decreasing, either directly or indirectly, an immune response against an antigen. A vaccine typically increases the immune response against an antigen.

Thus, in a first aspect, the present invention provides a universal H5N1 vaccine for the treatment or prevention of a disease in a subject, wherein the disease is associated with an H5N1 subtype of avian influenza virus. In one embodiment, the universal H5N1 vaccine comprises a prophylactically effective amount of a first immunogenic agent, a prophylactically effective amount of a second immunogenic agent and a prophylactically effective amount of a third immunogenic agent. In another embodiment, the subjects may be humans, domestic animals (dog; cat, monkey etc.); livestock (horse, cow, sheep, goat, pig etc.), wild birds (wild geese, wild ducks, etc.) and domestic birds (chicken, duck, geese etc.).

In one embodiment, each immunogenic agent comprises a hemagglutinin or antigenic portion thereof or a nucleic acid encoding the hemagglutinin or antigenic portion thereof. As used herein, antigenic portion of hemagglutinin refers to the portion of hemagglutinin that includes the neutralizing epitopes. In an additional embodiment, the antigenic portion includes an epitope of hemagglutinin. In a further embodiment, an immunogenic agent is virus comprising hemagglutinin. In another embodiment, the virus is inactivated. In an additional embodiment, the virus is an attenuated virus. In another embodiment, the virus is in the form of a virosome. In a further embodiment, the virus is egg-derived or cell culture-derived. In another embodiment, immunogenic agent is a split virus comprising hemagglutinin or a split virus antigenic preparation. In one embodiment, the immunogenic agent is hemagglutinin or antigenic portion thereof. In another embodiment, the hemagglutinin or antigenic portion thereof has been isolated. In an additional embodiment, the hemagglutinin or antigenic portion thereof is produced by a viral expression vector such that it is presented or displayed on the surface of the virus. In one embodiment, the viral expression vector is a baculovirus expression vector and the virus presenting or displaying the hemagglutinin or antigenic portion thereof is a baculovirus. In another embodiment, the viral expression vector such as a modified vaccinia virus expression vector, an, adenovirus expression vector, a poxvirus expression vector, and the like. In one embodiment, the immunogenic agent is a nucleic acid encoding the hemagglutinin or antigenic portion thereof which is capable of expression in the subject.

In one embodiment, the immunogenic agents may of the same class, e.g., they may all be inactivated viruses or baculoviruses presenting or displaying the hemagglutinin or antigenic portion thereof. In another embodiment, the immunogenic agents may be of different classes, e.g. the first immunogenic may be an inactivated virus, the second immunogenic agent may be a baculoviruses presenting or displaying the hemagglutinin or antigenic portion thereof and the third immunogenic agent may be the same as one of these two classes or a different class.

In accordance with the present invention a universal H5N1 vaccine is prepared in which the first immunogenic agent comprises hemagglutinin or an antigenic peptide thereof of the virus strain A/Indonesia/CDC669/2006 (H5N1), the second immunogenic agent comprises hemagglutinin or an antigenic peptide thereof of the virus strain A/Vietnam 1203/2004 (H5N1) and the third immunogenic agent comprises hemagglutinin or an antigenic peptide thereof of the virus strain A/Anhui/1/2005 (H5N1). As described herein, each immunogenic agent may be a virus, a protein, a peptide, a nucleic acid or the like that comprises or encodes the hemagglutinin or antigenic peptide thereof of the specified virus.

The immunogenic agents may be formulated into a composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic basis such as, for example, sodium, potassium, ammonium, calcium, or ferric hydroxides, and such organic basis as isopropylamine, trimethylamine, 2-ethylamino ethanol, histidine, procaine, and the like.

In general, suitable compositions may be prepared according to methods which are known to those of ordinary skill in the art and may include pharmaceutically acceptable diluents, adjuvants and/or excipients. The diluents, adjuvants and excipients must be "acceptable" in terms of being compatible with the other ingredients of the composition, and not deleterious to the recipient thereof.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions. Most preferably, the diluent is saline.

For administration as an injectable solution or suspension, non-toxic parenterally acceptable diluents or carriers can include, Ringer's solution, medium chain triglyceride (MCT), isotonic saline, phosphate buffered saline, ethanol and 1,2 propylene glycol. Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents. Adjuvants or immunostimulatory components useful in the preparation of the compositions include, and are not limited to, aluminum salts, mineral oils, Mycobacterial products (e.g., Freund's complete or incomplete adjuvants) or vehicles such as a mixture of the plant glycoside saponin, cholesterol and phosphatidylcholine that provides a vehicle for presentation of several copies of the protein on a cage-like structure. For purposes of this specification, an adjuvant is a substance that accentuates, increases, moderates or enhances the immune response to an immunogen or antigen. Adjuvants typically enhance both the humor and cellular immune response but an increased response to either in the absence of the other qualifies to define an adjuvant. Moreover, adjuvants and their uses are well known to immunologists and are typically employed to enhance the immune response when doses of immunogen are limited, when the immunogen is poorly immunogenic, or when the route of administration is sub-optimal. Thus the term "adjuvating amount" is that quantity of adjuvant capable of enhancing the immune response to a given immunogen or antigen. The mass that equals an "adjuvating amount" will vary and is dependant on a variety of factors including, but not limited to, the characteristics of the immunogen, the quantity of immunogen administered, the host species, the route of administration, and the protocol for administering the immunogen. The "adjuvating amount" can readily be quantified by routine experimentation given a particular set of circumstances. This is well within the ordinarily skilled artisan's purview and typically employs the use of routine dose response determinations to varying amounts of administered immunogen and adjuvant. Responses are measured by determining serum antibody titers or cell-mediated responses raised to the immunogen using enzyme linked immunosorbant assays, radio immune assays, hemagglutination assays and the like.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E5 alpha-tocopherol, ascorbic acid, methyl paraben, propyl paraben or sodium bisulphite. Suitable lubricants include magnesium stearate, stearic acid, sodium oleate, sodium chloride or talc.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like. Emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington: The Science and Practice of Pharmacy, 21st Ed., Ed. D. B. Troy, Lippincott, Williams & Wilkins, Baltimore, 2006, hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Preparation of the compositions uses routine methods known to persons skilled in the art. Typically, such compositions are prepared as injectables, either as liquid solutions or suspensions; solid forms suitable for solution in, or suspension in, liquid prior to injection may also be prepared. The preparation may also be emulsified. The active immunogenic ingredients are often mixed with excipients that are pharmaceutically acceptable and compatible with the active ingredient.

In a second aspect, the present invention provides a method for modulating an immune response to an avian influenza virus which comprises administering to a subject a prophylactically effective amount of a universal H5N1 vaccine. The universal H5N1 vaccine is as described above. Although it is preferred that the universal H5N1 vaccine be administered as a single composition, it is also contemplated that the individual components of the vaccine could be separately but contemporaneously administered to the subject.

According to the methods of present invention, vaccines and compositions may be administered by any suitable route, either systemically, regionally or locally. The particular route of administration to be used in any given circumstance will depend on a number of factors, including the nature of the disease to be treated, the severity and extent of the disease, the required dosage of the particular compounds to be delivered and the potential side-effects of the desired vaccines or compositions.

For example, in circumstances where it is required that appropriate concentrations of the desired vaccines or compositions are delivered directly to the site to be treated, administration may be regional rather than systemic. Regional administration provides the capability of delivering very high local concentrations of the desired vaccines or compositions to the required site and thus is suitable for achieving the desired therapeutic or preventative effect whilst avoiding exposure of other organs of the body to the vaccines or compositions and thereby potentially reducing side effects. By way of example, administration according to embodiments of the invention may be achieved by any standard routes, including intracavitary, intravesical, intramuscular, intraarterial, intravenous, subcutaneous, topical or oral. Intracavitary administration may be intraperitoneal or intrapleural.

If desired, devices or compositions containing the immunogenic agents suitable for sustained or intermittent release could be, in effect, implanted in the body or topically applied thereto for the relatively slow release of such materials into the body.

Administration of an expression vector or host cell may include delivery via direct oral intake, systemic injection, or delivery to selected tissue(s) or cells, or indirectly via delivery to cells isolated from a subject or a compatible donor. With regard to nucleic acid based compositions, all modes of delivery of such compositions are contemplated by the present invention.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are well known in the art.

The effective dose level of the administered compound for any particular subject will depend upon a variety of factors including: the type of disease being treated and the stage of the disease; the activity of the compound employed; the composition employed; the age, body weight, general health, sex and diet of the subject; the time of administration; the route of administration; the rate of sequestration of compounds; the duration of the treatment; drugs used in combination or coincidental with the treatment, together with other related factors well known in the art.

In a third aspect, the present invention provides a method for the prevention or treatment of a disease associated with an avian influenza virus which comprises administering to a subject a prophylactically effective amount of a universal H5N1 vaccine. The universal H5N1 vaccine is as described above. Suitable compositions, administration and dosages are as described above.

In a fourth aspect, the present invention provides use of a universal H5N1 vaccine for modulating an immune response to an avian influenza virus. The universal H5N1 vaccine is as described above.

In a fifth aspect, the present invention provides use of a universal H5N1 vaccine for the treatment of a disease associated with an avian influenza virus. The universal H5N1 vaccine is as described above.

Methods for preparing and administering vaccines are well known in the art and are exemplified by U.S. Pat. Nos. 7,510,719, 7,537,768, 7,666,439 and 7,691,368; U.S. Patent Application Publication Nos. 2008/0187557, 2009/0136532, 2009/0263422, 2009/0304730, 2010/0047271, 2010/0074916 and 2010/0086485; and International Application Publication Nos. WO 2007/129984, WO 2008/048984, WO 2008/115314, WO 2009/069447, WO 2009/115917, WO 2010/021289 and WO 2010/036948, each incorporated herein by reference.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Viruses: H5N1 human influenza viruses from clade 2.1 A/Indonesia/CDC669/2006, A/Indonesia/TLL013/2006 and one avian strain A/Indonesia/TLL014/2006 were obtained from the Ministry of Health (MOH), Republic of Indonesia. The avian H5N2 subtype obtained from the Agri-Food and Veterinary Authority (AVA) of Singapore. The H5N1 viruses from different phylogenetic clades/subclades (Table 1) were rescued by Reverse Genetics [WHO, 2004]. Briefly, the hemagglutinin (HA) and neuraminidase (NA) genes of H5N1 viruses from clades 1, 2.1, 2.2, 2.3, 4, 7 and 8 were synthesized (GenScript, USA) based on the sequence from the NCBI influenza Database. The synthetic HA and NA genes were cloned into a dual-promoter plasmid for influenza A reverse genetics (Prabakaran et al., 2009). The dual-promoter plasmids were obtained from Center for Disease Control and Prevention, Atlanta, Ga., USA. Reassortant viruses were rescued by transfecting plasmids containing HA and NA along with the remaining six influenza genes derived from high-growth master strain A/Puerto Rico/8/34 (H1N1) into co-cultured 293T and MDCK cells using Lipofectamine 2000 (Invitrogen Corp.). At 72 h post-transfection the culture medium was inoculated into embryonated eggs or MDCK cells. The HA and NA genes of reassortant viruses from the second passage were sequenced to confirm presence of introduced HA and NA genes and the absence of mutations. Stock viruses were propagated in the allantoic cavity of 11 day-old embryonated eggs, virus containing allantoic fluid was harvested and stored in aliquots at −80 C. Virus content was determined by standard hemagglutination (HA) assay. All experiments with highly pathogenic viruses were conducted in a biosafety level 3 (BSL-3) containment facility in compliance with CDC/NIH and WHO recommendations.

TABLE 1

Reassortant Influenza A Viruses Generated from Reverse Genetics.

| Serial No. | Viruse name (subtype) | Clade | Host |
|---|---|---|---|
| 1 | A/Vietnam 1203/04 (H5N1) | 1 | Human |
| 2 | A/Indonesia/CDC1031/07 (H5N1) | 2.1 | Human |
| 3 | A/turkey/Turkey1/05*(H5N1) | 2.2 | Avian |
| 4 | A/Anhui/1/05*(H5N1) | 2.3 | Human |
| 5 | A/chicken/Shanxi/2/06 (H5N1) | 7 | Avian |
| 6 | A/goose/Guiyang/337/06 (H5N1) | 4 | Avian |
| 7 | A/chicken/Henan/12/04 (H5N1) | 8 | Avian |

Neutralizing monoclonal antibodies (n-mAbs): A panel of five different neutralizing mAbs against the HA of H5N1 viruses were selected for the characterization of the escape mutants. Briefly, BALB/c mice were immunized twice 2 weeks apart by subcutaneous injection with purified formalin inactivated A/Indonesia/CDC669/2006 or A/Indonesia/TLL014/2006 or A/Chicken/Singapore/98 H5N2 antigen mixed with adjuvant (SEPPIC, France). Mice received an additional intravenous injection of same viral antigen, 3 days before the fusion of splenocytes with SP2/0 cells (Yokoyama, 2004).

Mapping of H5HA neutralizing epitopes by using n-mAbs: The major neutralizing epitopes of H5 were mapped by characterization of escape mutants (Kaverin et al., 2007) with five different neutralization monoclonal antibodies (6B8, 4C2, 2D9, 4F8 and 3H11). Briefly, H5N1 viruses were incubated with an excess amount of n-mAb for 1 h and the mixture was inoculated into 11-day old embryonated chicken eggs. The eggs were incubated at 37° C. for 48 h. Virus was harvested and used for cloning in limiting dilution in embryonated chicken eggs and the escape mutants were plaque purified. Mutations in a HA gene were then identified by sequencing and compared with the sequence of the parent virus.

Epitope distribution analysis: Neutralizing epitopes of H5HA identified by Kaverin et al. (2007), along with major epitopes identified in this study, were taken into consideration for sequence analysis. To analyze the distribution of the neutralizing epitopes among the H5N1 viruses, full-length HA sequences were compared with avian and human H5N1 viruses from NCBI influenza database. The protein polymorphism of H5N1 was analyzed with Influenza Research Database (Fludb.org) and up to 317 human strains and 2028 avian strains were aligned in this study. To assess variation in the epitopes, positional frequency tables were produced from multiple sequence alignments for each H5N1 viruses.

Selection of vaccine strains: Three different H5N1 strains were selected to cover the variations within the neutralizing epitopes of HA among most H5N1 lineages. Further, the reactivity of the selected vaccine strains was confirmed by hemagglutination inhibition assay and microneutralization assay using appropriate neutralizing monoclonal antibodies.

Generation of recombinant baculovirus: For the generation of recombinant baculovirus vectors, as described previously, WSSV ie1 promoter controlled HA expression cassette were inserted into the shuttle vector pFastBac1 and integrated into the baculovirus genome within DH10BAC™ according to the protocol of Bac-To-Bac system (Invitrogen). Briefly, the full length HA gene was amplified from three different influenza strains in a standard PCR method (94° C. 20 sec, 55° C. 30 sec and 72° C. 2 min for 30 cycles). H5HA sequences were amplified with primers H5FSal 5' ACGCGTCGACATGGAGAAAATAGTGC TTCT 3' (SEQ ID NO:1) and H5RNot 5' ATAAGGCGGCCGCTTAAAT-GCAAATTCTGCA TTG 3' (SEQ ID NO:2) from H5N1 viruses—A/Indonesia/CDC669/2006(H5N1) (GenBank Accession Nos. CY014481 and ABI36428; SEQ ID NO:3 (nucleotide sequence) and SEQ ID NO:4 (amino acid sequence); A/Viet Nam/1203/2004(H5N1) (GenBank Accession Nos. EU122404 and ABW90135; SEQ ID NO:5 (nucleotide sequence) and SEQ ID NO:6 (amino acid sequence); and A/Anhui/1/2005(H5N1) (GenBank Accession Nos. DQ371928 and ABD28180; SEQ ID NO:7 (nucleotide sequence) and SEQ ID NO:8 (amino acid sequence). WSSV ie1 promoter was inserted into vector with SnabI and SalI sites and HA genes were inserted into pFastBac1 vector with the NotI-SalI site. After transformation of transfer vectors into DH10BAC, recombinant bacmids were transfected into Sf9 cells, and the budded baculovirus particles released into the medium were harvested at 4 days post-transfection.

Vaccine trial: Specific-pathogen-free female BALB/c mice (6 weeks old) were obtained from the Laboratory Animals Centre, National University of Singapore, and maintained at the Animal Holding Unit of the Temasek Life Sciences Laboratory. Twenty four mice per each experimental group (n=24/group) were vaccinated subcutaneously two times at a regular interval of 28 days with 100 µA of baculovirus displaying HA of H5N1-A/VietNam/1203/2004 (Mono-BacHA) or as a mixture of each baculovirus displaying HA from A/Indonesia/CDC669/2006-H5N1, A/Viet Nam/1203/2004-H5N1 A/Anhui/1/2005-H5N1 (Tri-BacHA) with or without adjuvant, Montanide ISA563 (water in oil emulsion) (SEPPIC, France). Also, inactivated RG-H5N1 virus (A/VietNam/1203/2004-H5N1) was used as a reference vaccine control. The serum was collected from ten mice per experimental group on day 14, 28 and day 42. Hemagglutination inhibition assay and indirect ELISA was performed to asses the HA specific antibody response. In addition, serum cross-clade neutralizing capacity was measured by microneutralization assay. The efficacy of the vaccine was assessed by host challenge against HPAI H5N1 influenza strains from different clades. All animal experiments were carried out in accordance with the Guides for Animal Experiments of the National Institute of Infectious Diseases (NIID), and experimental protocols were reviewed and approved by Institutional Animal Care and Use Committee of the Temasek Life Sciences Laboratory, National University of Singapore, Singapore.

Hemagglutination inhibition assay: Hemagglutination inhibition assays were performed as described previously (Webster et al., 1991). Receptor-destroying enzyme (RDE)-treated sera were serially diluted (2-fold) in V-bottom 96-well plates. Approximately 4 HA units of viral antigen was incubated with the serum for 30 min at room temperature, followed by the addition of 1% chicken red blood cells (RBCs) and incubation at room temperature for 40 min.

Microneutralization assay: The microneutralization test was performed according to a previously described protocol (Suguitan et al., 2006). Briefly, MDCK cells were seeded in 96-well culture plates and cultured at 37° C. to form a monolayer. Serial 2-fold dilutions of heat-inactivated (56° C. for 45 min) serum samples were mixed separately with 100 50% tissue culture infective doses (TCID50) of H5N1 virus from different clades and incubated at room temperature for 1 h, and the mixtures were added to a monolayer of MDCK cells in triplicate wells. The neutralizing titers of mouse antiserum that completely prevented any cytopathic effect at reciprocal dilutions were calculated.

Diseases challenge test against H5N1 virus infection: Three-weeks after final vaccination, mice were transferred into animal BSL3 containment facility. Six mice per group were challenged intranasally with 5MLD50 (Mouse lethal dose 50%) of homologous (A/Vietnam/1203/2004(H5N1) clade 1.0) and heterologous clade 2.1 (A/Indonesia/TLL13/2006(H5N1)) and clade 7.0 (A/chicken/Shanxi/2/06) HPAI H5N1 strains. Fifty percent mouse lethal dose (MLD50) of the influenza virus required for intranasal challenge experiments was predetermined. Mice were observed daily to monitor body weight and mortality. Monitoring continued until all animals died or until day 14 after challenge. For histopathology, mice were necropsied and the lungs were stored in 10% (wt/vol) neutral buffered formalin and embedded in paraffin and sectioned. Sections were stained with hematoxylin and eosin (H/E) prior to light microscopy examination and were evaluated for lung pathology. All challenge experiments were conducted at animal biosafety level 3 containment facility.

Example 2

Identification and Characterization of Neutralizing Epitopes of H5HA Using n-mAbs A panel of five different neutralizing mAbs (6B8, 4C2, 2D9, 4F8 and 3H11) against influenza hemagglutinin (HA) was produced previously in our laboratory. All n-mAbs recognized the conformational epitopes of H5 and possessed the ability to neutralize the influenza virus infection in vitro. Also, these n-mAbs has been confirmed to have hemagglutination inhibition activity (data not shown). Amino acids involved in forming the epitopes of n-mAbs were analysed using virus escape mutants. Sequencing of the complete HA gene isolated from multiple escape variants (a) to n-mAb 6B8 carried a single point mutations at amino acid positions 189 (Lys to Asn) or 155 (Asn to Asp), (b) to n-mAb 4F8 carried a single point mutations at amino acid position 155 (Asn to Asp) and (c) to n-mAb 2D9 carried a single point mutations at amino acid positions 189 (Arg to Trp) or 223 (Ser to Arg). Similar analysis for n-mAb 4C2 revealed the involvement of amino acid 155 (Ser to Ile) or 189 (Arg to Lys) in forming the epitope while n-mAb 3H11 carried a single point mutations at amino acid position 138 "Leu", 139 "Gly" and 140 "Ser." All amino acid positions indicated here excludes the signal peptide of HA. See SEQ ID NOs:9-11 for the amino acid sequences of the mature HA proteins for A/Indonesia/CDC669/2006(H5N1), A/Viet Nam/1203/2004 (H5N1) and A/Anhui/1/2005(H5N1), respectively.

Example 3

Epitope Distribution Analysis

Full length HA sequences of avian and human H5N1 viruses were obtained from the Influenza Virus Database maintained by the National Center for Biotechnology Information. HA sequences of human and avian H5N1 isolates were compared with the major neutralizing epitope sequences (amino acid position 138, 140, 155, 189, 159, 194 and 218 of the HA1 region). The results revealed that most of the major antigenic epitope regions contained significant variations among the human as well as avian H5N1 lineages (Table 2). Analysis of the highly variant 140's loop (140 aa) indicated the predominant presence of amino acid "Lys" (22.5%) and "Ser" (28.5%) at this position in all H5N1 human isolates, with only minor presence of "Thr" at position 140 (6%) (Table 2). Further, the 155 aa of 150's loop has only two variants (63.4% of human H5N1 isolates have amino acid "Ser" and remaining 34.4% have amino acid "Asn" at this position). Also, amino acid at position 189 on influenza hemagglutinin, located in the receptor binding site, contains amino acid "Arg" in 64.26% of all H5N1 human strains while remaining 34.65% have amino acid "Lys" at this position (Table 2).

TABLE 2

Epitope Frequency in H5N1 Strains

| | Human H5N1 | | | Avian H5N1 | | |
|---|---|---|---|---|---|---|
| 138th aa | Gln 58.9% | | Leu 41.1% | Gln 80.4% | | Leu 13.6% |
| 140th aa | Lys 22.5% | Ser 28.5% | Thr 6% | Lys 34.8% | Ser 6% | Thr 16.6% |
| 155th aa | Asn 34.4% | | Ser 63.4% | Asn 50.6% | | Ser 43.2% |
| 189th aa | Arg 64.3% | | Lys 34.7% | Arg 43.3% | | Lys 55.1% |
| 159th aa | Thr 99.7% | | | Thr 98.4% | | |
| 194th aa | Pro 100% | | | Pro 98% | | |
| 218th aa | Lys 99.7% | | | Lys 99.2% | | |

Example 4

Selection of Vaccine Strains

Based on the amino acid sequence analysis within the neutralizing epitopes, panel of H5N1 viruses (317 human strains and 2028 avian strains) were analyzed for the frequency of amino acid variations within the major neutralizing epitopes of HA. We have selected three different H5N1 strains (A/Indonesia/CDC669/2006(H5N1) (clade 2.1), A/Viet Nam/1203/2004(H5N1) (clade 1.0) and A/Anhui/1/2005(H5N1) (clade 2.3)), such that the combination of these strains would cover all major amino acid variations of neutralizing epitopes of the H5HA (Table 3). For example, A/Viet Nam/1203/2004(H5N1) and A/Indonesia/CDC669/2006(H5N1) strain contain "Ser" at position 155 while A/Anhui/1/2005(H5N1) strain has "Asn" at the same position. Further, A/Viet Nam/1203/2004(H5N1) and A/Anhui/1/2005(H5N1) strain contain "Lys" at position 189 while the A/Indonesia/CDC669/2006(H5N1) strain has an amino acid "Arg" at the same position (Table 3).

TABLE 3

Immunogenic Epitopes in the Three Strains

| Name | Clade | 138 | 140 | 155 | 189 | 194 | 159 | 218 | host |
|---|---|---|---|---|---|---|---|---|---|
| A/Vietnam/1203/2004 (H5N1) | 1 | Gln | Lys | Ser | Lys | Pro | Thr | Lys | Human |
| A/Indonesia/CDC669/2006 (H5N1) | 2.1 | Leu | Ser | Ser | Arg | Pro | Thr | Lys | Human |
| A/Anhui/1/2005(H5N1) | 2.3 | Gln | Thr | Asn | Lys | Pro | Thr | Lys | human |

Example 5

Differential Recognition of Selected Vaccine Strains by n-mAbs

The variations within the selected vaccine strains (A/Vietnam/1203/2004(H5N1) (clade 1.0), A/Indonesia/CDC669/2006(H5N1) (clade 2.1) and A/Anhui/1/2005(H5N1) (clade 2.3)) were confirmed based on the results of virus neutralization and hemagglutination inhibition (HI) with different n-mAbs. Exposure of vaccine strains to n-mAbs resulted in differential reactivity pattern with n-mAbs. As shown in Table 4A and 4B, n-mAb 6B8 shows preferential binding to the A/Vietnam/1203/2004(H5N1) and the A/Anhui/1/2005 (H5N1) strains while neutralization of A/Indonesia/CDC669/2006(H5N1) by the same n-mAb is absent as indicated by hemagglutination inhibition and microneutralization assay. However, n-mAb 4C2 neutralizes only A/Indonesia/CDC669/2006(H5N1) strain. Similar difference in the pattern of recognition was observed with other n-mAbs. These findings also indicated the existence of strong antigenic variance between the A/Indonesia/CDC669/2006(H5N1) and the A/Vietnam/1203/2004(H5N1) strains (Table 4A and 4B). In addition, inclusion of A/Anhui/1/2005 (H5N1) in vaccine composition covers the variation of amino acid at position 155 (Asn) of vaccine strains, which comprises 34% of human H5N1 isolates.

TABLE 4A

Hemagglutination Inhibition Against the Three H5N1 Strains with n-mAbs (1 mg/ml)

| n-mAb | A/Vietnam/1203/ 2004 (H5N1) | A/Indonesia/CDC669/ 2006 (H5N1) | A/Anhui/1/ 2005 (H5N1) |
| --- | --- | --- | --- |
| 6B8 | 512 | <8 | 256 |
| 4C2 | <8 | 512 | <8 |
| 4F8 | 64 | 512 | 32 |
| 3H11 | <8 | 512 | <8 |
| 2D9 | 128 | 512 | 128 |

TABLE 4B

Virus Microneutralization Against the Three H5N1 Strains with n-mAbs (1 mg/ml)

| n-mAb | A/Vietnam/1203/ 2004 (H5N1) | A/Indonesia/CDC669/ 2006 (H5N1) | A/Anhui/1/ 2005 (H5N1) |
| --- | --- | --- | --- |
| 6B8 | 320 | <10 | 160 |
| 4C2 | <10 | 320 | <10 |
| 4F8 | 40 | 320 | 20 |
| 3H11 | <10 | 320 | <10 |
| 2D9 | 80 | 320 | 160 |

Example 6

Serum Hemagglutination Inhibition (HI) Assay

Hemagglutination inhibition titers, which measures the efficacy of the antibody response to inhibit the functional ability of HA (A/Vietnam/1203/2004(H5N1)), was also obtained. The HI titers results showed that mice immunized with adjuvanted Tri-BacHA significantly enhanced the serum HI titre when compared to the unadjuvanted Tri-BacHA on day 28 and 42 (FIG. 1).

Moreover, HI titer of mice vaccinated with adjuvanted Tri-BacHA was comparable to the HI titer of mice vaccinated with either adjuvanted RG-H5N1 virus or adjuvanted with Mono-BacHA (FIG. 1).

Example 7

Serum Cross-Clade Neutralizing Antibody Titers

Figures 2A, 2B:
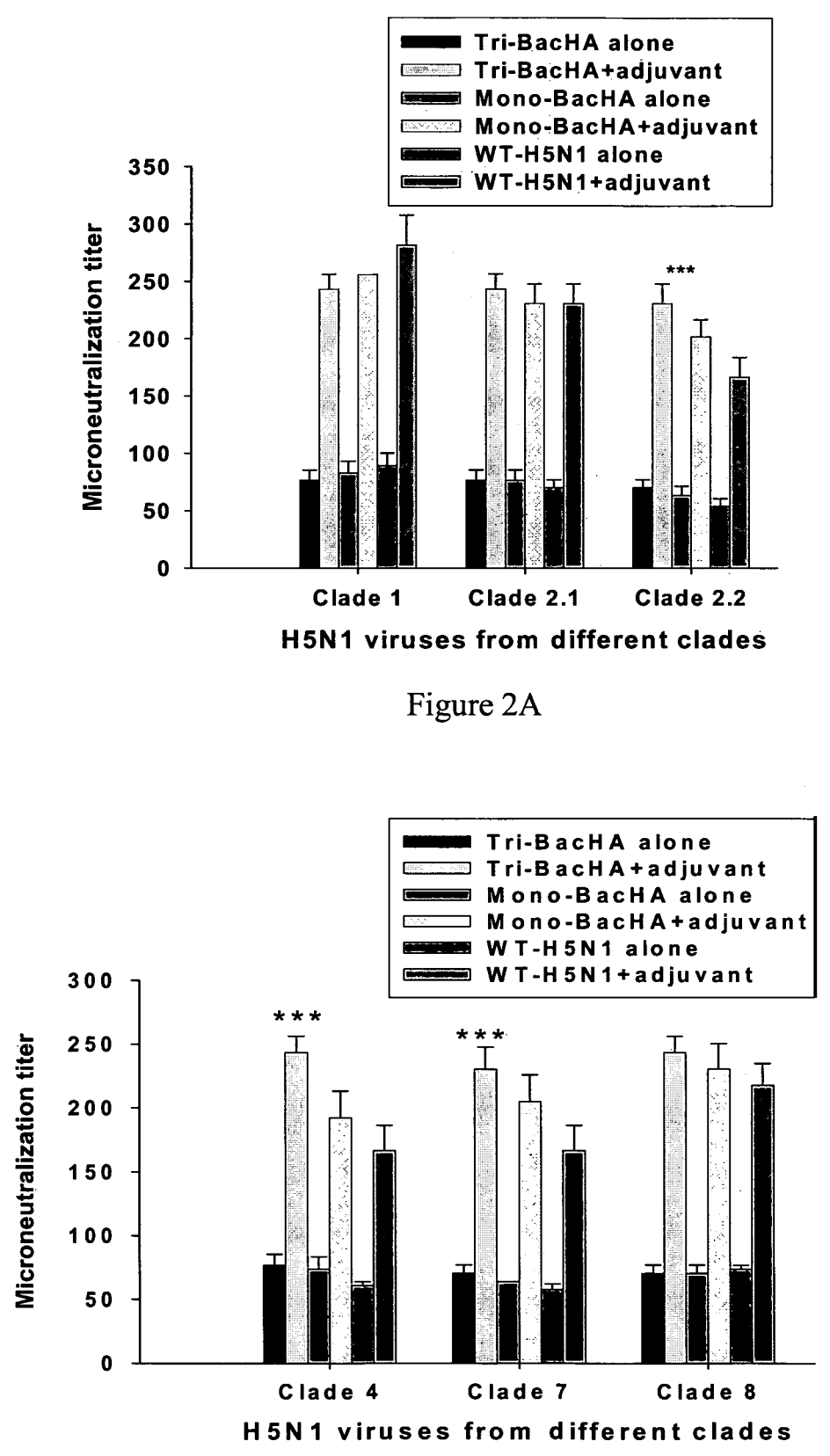

The serum neutralizing antibody titer against 100 TCID50 of different clades of H5N1 strains on day 42 showed that vaccination with adjuvanted Tri-BacHA significantly neutralized viruses from different clades (clade 1.0, clade 2.1, clade 2.2, clade 4.0, clade 7.0 and clade 8.0) compared with mice vaccinated with unadjuvanted Tri-BacHA (FIGS. 2A and 2B).

Moreover, mice immunized with adjuvanted Tri-BacHA significantly enhanced neutralization titer against clade 2.2, clade 4 and clade 7 when compared to mice vaccinated with adjuvanted vaccines: RG-H5N1 or Mono-BacHA vaccine (FIGS. 2A and 2B). Further, vaccine composition containing Mono-BacHA or RG-H5N1, both adjuvanted with Seppic, was able to neutralize clade 1 (homologous), clade 2.1 and clade 8.0 but did not result in efficient neutralization against other clades (clade 2.2, clade 4.0 and clade 7.0 H5N1 strains).

Example 8

Challenge Studies after Vaccination

Figure 3:
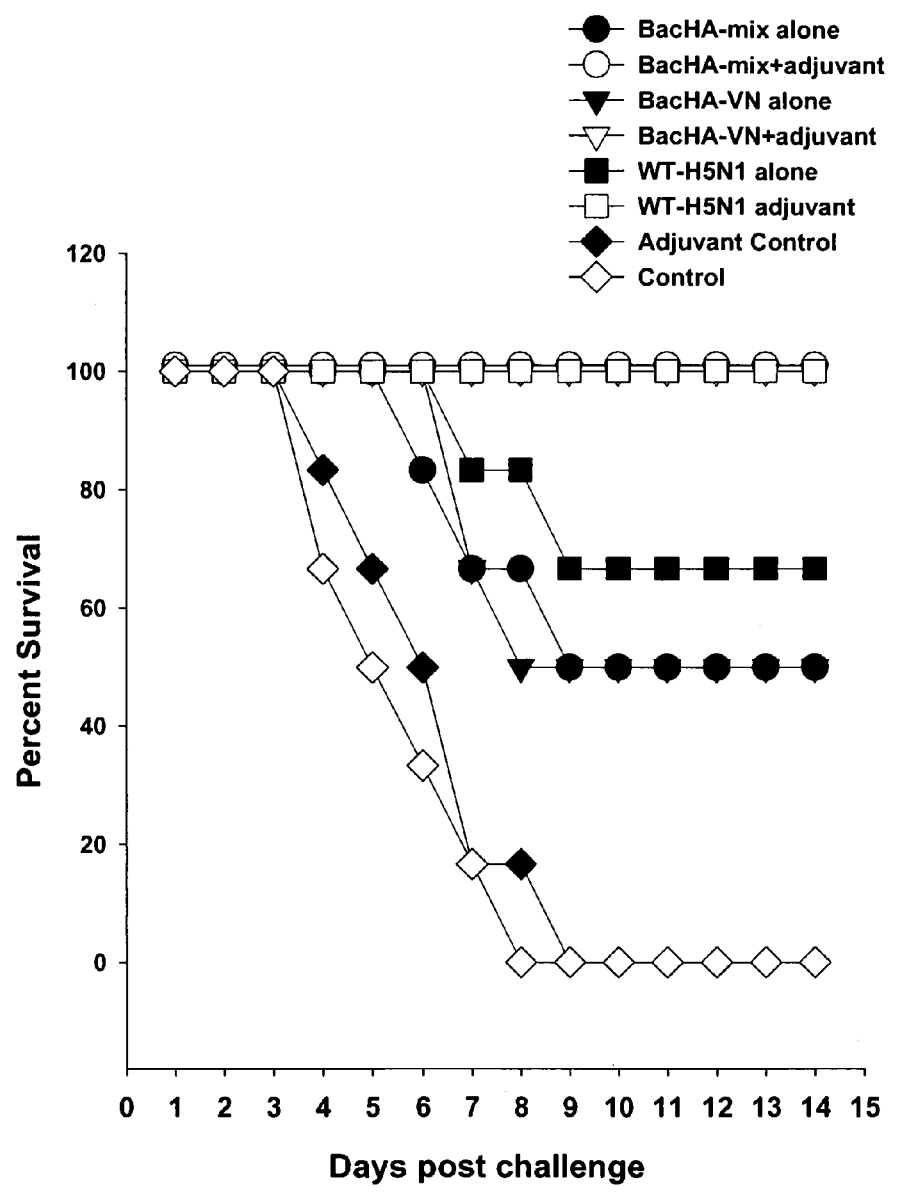
Figure 4:
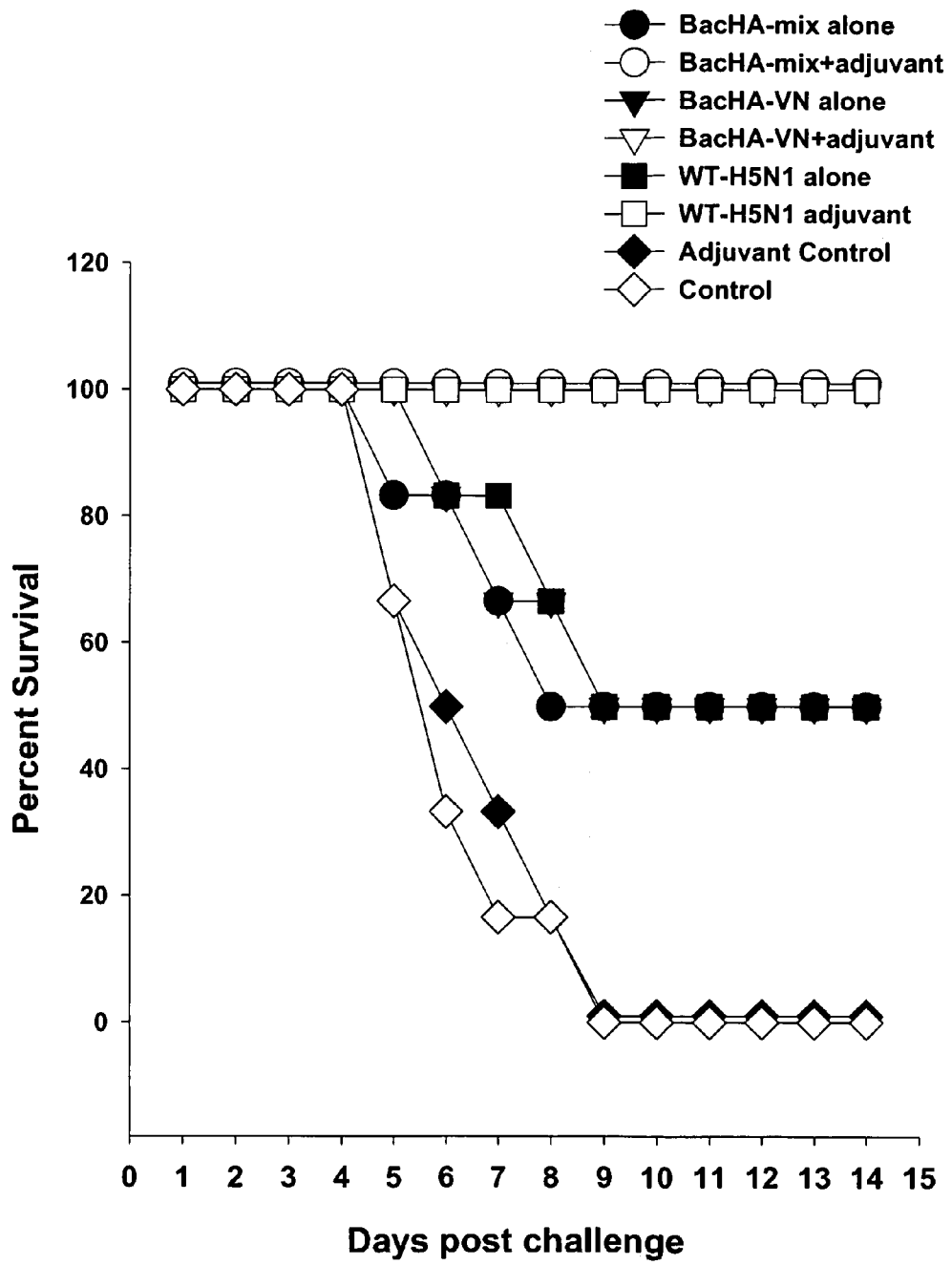
FIG. 4 show protection of mice from lethal H5N1 viral challenge. Groups of mice were subcutaneously immunized two times on days 0 and 28 with three strains of BacHA (Tri-BacHA) or single strain (A/Vietnam/1203/2004 (H5N1)) of BacHA (Mono-BacHA) or inactivated whole H5N1 viral vaccine (WT-H5N1). Three weeks after the final vaccination, mice were intranasally infected with 5MLD50 (Mouse lethal dose 50%) of clade 2.1 (A/Indonesia/TLL013/2006(H5N1)) HPAI H5N1 strains. Mice were monitored for survival throughout a 14 day observation period. The results are expressed in terms of percent survival.
Figure 6:
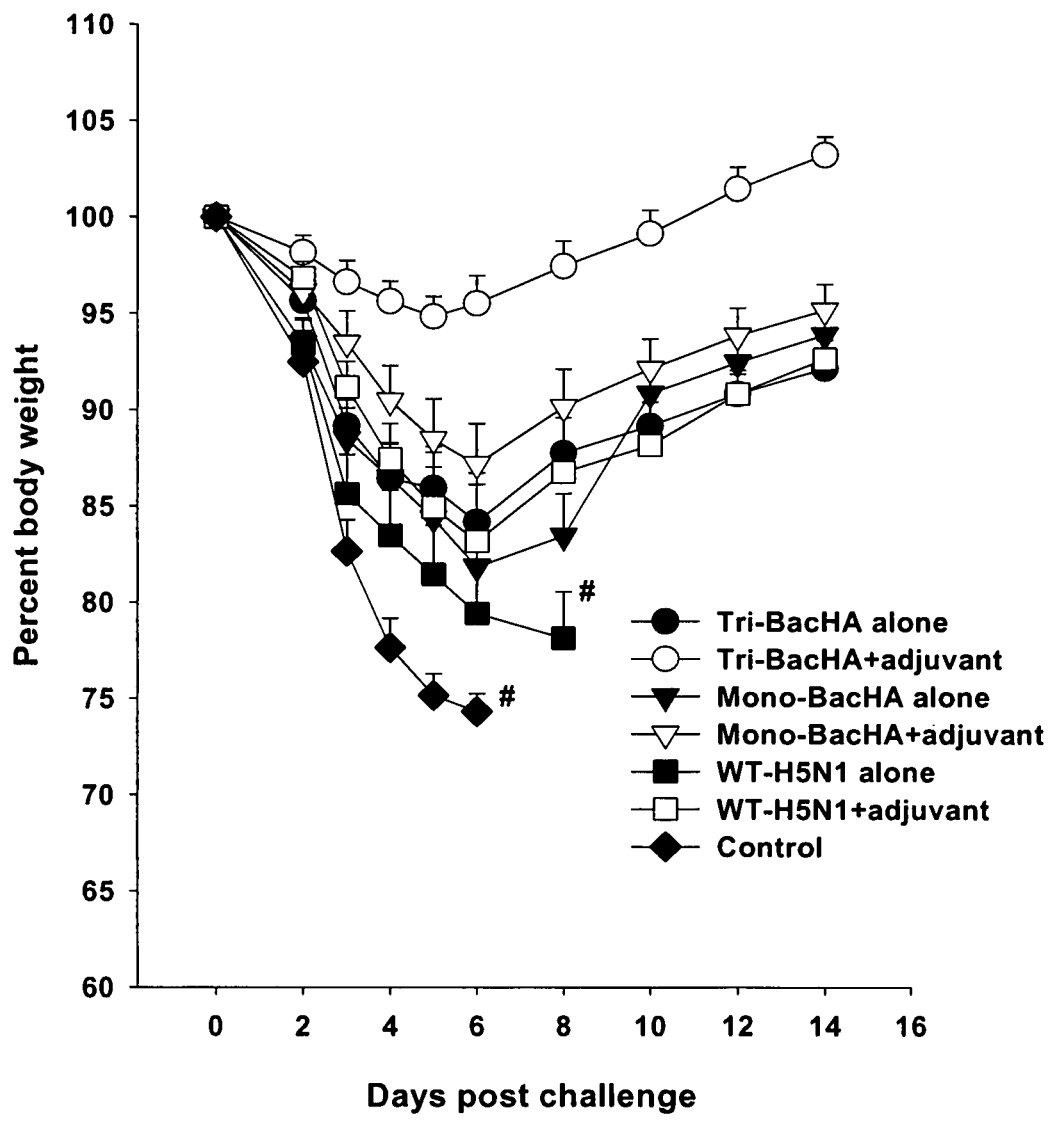

Three weeks after final immunization, all groups of mice were challenged intranasally with 5 $MLD_{50}$ of HPAI H5N1 strains from clade 1.0 or clade 2.1 or clade 7.0. Groups of mice immunized with adjuvanted Tri-BacHA or Mono-BacHA or RG-H5N1 obtained 100% protection against clade 1.0 and clade 2.1 (FIG. 3 and FIG. 4). Moreover, adjuvanted Tri-BacHA provided 100% protection against clade 7.0 H5N1 infection. However, mice immunized with adjuvanted RG-H5N1 vaccine and Mono-BacHA vaccine provided only 66.6% and 83.3% protection against clade 7.0 H5N1 infection, respectively (FIG. 6).

Figure 5:
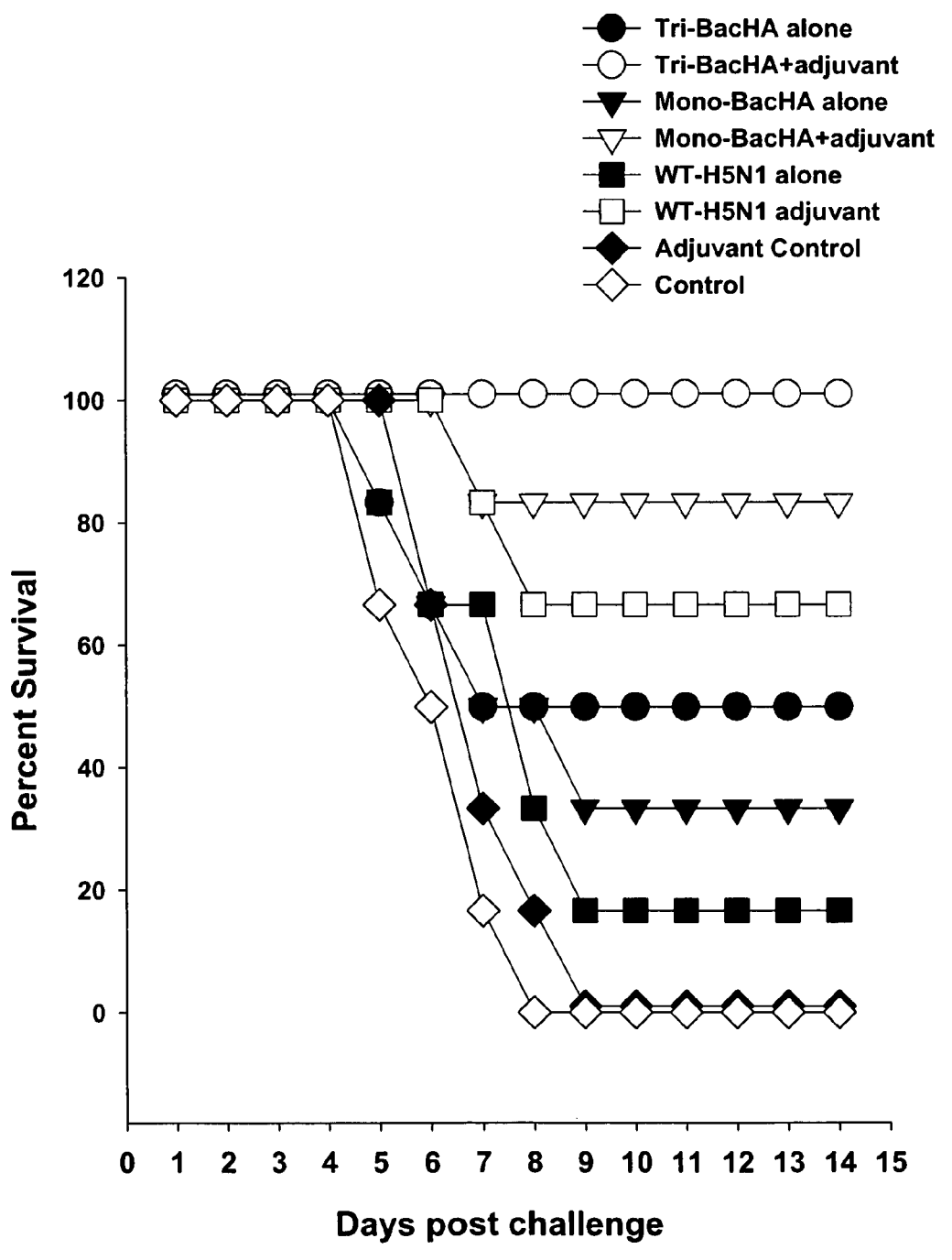

The progression of infection was indicated by varying trends of decrease in body weight in the different groups. In groups of mice challenged with H5N1 clade 7.0 (A/chicken/Shanxi/2/06(H5N1)) strain, no significant decreases in body weight was observed in mice vaccinated with adjuvanted Tri-BacHA after the challenge (FIG. 5). However, mice vaccinated with Mono-BacHA with adjuvant showed up to 12% loss of bodyweight though the bodyweight is gradually regained after 6 days post challenge. The groups that were vaccinated with adjuvanted RG-H5N1 vaccine showed a higher loss of body weight of up to 17% on day 6, which is then regained slowly on day 14 after challenge (FIG. 5).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Ayora-Talayera G, Shelton H, Scull M A, Ren J, Jones I M, et al. (2009). Mutations in H5N1 Influenza Virus Hemagglutinin that Confer Binding to Human Tracheal Airway Epithelium. PLoS ONE 4(11): e7836.

Chen G L, Subbarao. K. Attacking the flu: Neutralizing antibodies may lead to universal' vaccine. Nat Med 15: 1251-1252.

Copeland, C S, Doms, R W, Bolzau, E M, Webster, R G, and Helenius, A. 1986. Assembly of influenza hemagglutinin trimers and its role in intracellular transport. J. Cell Biol. 103: 1179-1191.

Gerhard W, Mozdzanowska K, Zharikova D. (2006). Prospects for universal influenza virus vaccine. Emerg Infect Dis 12:569-574.

Kaverin N V, Rudneva I A, Ilyushina N A, Varich N L, Lipatov A S, et al. (2002). Structure of antigenic sites on the hemagglutinin molecule of H5 influenza virus and phenotypic variation of escape mutants. J Gen Virol 83: 2497-2505.

Kaverin N V; Rudneva I A, Govorkova E A, Timofeeva T A, Shilov A A, Kochergin-Nikitsky K S, Krylov P S, Webster R G. (2007). Epitope mapping of the hemagglutinin molecule of a highly pathogenic H5N1 influenza virus by using monoclonal antibodies. J. Virol. 81, 12911-12917.

Lam T T, Hon C C, Pybus O G, Kosakovsky Pond S L, Wong R T, Yip C W, Zeng F, Leung F C. 2008. Evolutionary and transmission dynamics of reassortant H5N1 influenza virus in Indonesia. PLoS Pathog. 4, e1000130.

Manzoli L, Schioppa F, Boccia A, Villari P. (2007). The efficacy of influenza vaccine for healthy children: a meta-analysis evaluating potential sources of variation in efficacy estimates including study quality. Pediatr. Infect. Dis. J. 26: 97-106.

Plotkin J B, Dushoff J, Levin S A. 2002. Hemagglutinin sequence clusters and the antigenic evolution of influenza A virus. Proc Natl Acad Sci USA, 99(9):6263-6268.

Prabakaran M, Ho H T, Prabhu N, Velumani S, Szyporta M, et al. (2009). Development of epitope-blocking ELISA for universal detection of antibodies to human H5N1 influenza viruses. PLoS ONE 4: e4566.

Suguitan A L, Jr McAuliffe J, Milis K L, Jin H, Duke G, Lu B, Luke C J, Murphy B, Swayne D E, Kemble G, Subbarao K. 2006. Live, attenuated influenza A H5N1 candidate vaccines provide broad cross protection in mice and ferrets. PLoS Med. 3:e360.

Webster R G, Kawaoka Y, Taylor J, Weinberg R, Paoletti E. (1991). Efficacy of nucleoprotein and hemagglutinin antigens expressed in fowlpox virus as vaccine for influenza in chickens. Vaccine 9:303-308.

WHO (2005). Evolution of H5N1 Avian Influenza Viruses in Asia. Emerg Infect Dis 11:1515-1521.

Wu F, Huang J H, Yuan X Y, Huang W S, Chen Y H. (2007). Characterization of immunity induced by M2e of influenza virus. Vaccine 25: 8868-73.

Yokoyama W M (2004). Production of monoclonal antibody. Current Protocols in Immunology. Coligan J E, Kruisbeek A M, Margulies D H, Shevach E M, Strober W, eds. Newcastle, United Kingdom: John Wiley & Sons. Inc. pp 2.5.1-2.5.17.

The invention claimed is:

1. A universal H5N1 vaccine composition comprising a prophylactically effective amount of a first immunogenic agent or a nucleic acid encoding said first immunogenic agent, a prophylactically effective amount of a second immunogenic agent or a nucleic acid encoding said second immunogenic agent, a prophylactically effective amount of a third immunogenic agent or a nucleic acid encoding said third immunogenic agent, an adjuvant and a pharmaceutically acceptable carrier, wherein each of the first, second and third immunogenic agents comprises a virus selected from the group consisting of baculovirus, vaccina virus, adenovirus, and pox virus, wherein the virus presents or displays a full length hemagglutinin, wherein the first immunogenic agent comprises full length hemagglutinin of the virus strain A/Indonesia/CDC669/2006 (H5N1), wherein the second immunogenic agent comprises full length hemagglutinin of the virus strain A/Vietnam1203/2004 (H5N1), wherein the third immunogenic agent comprises full length hemagglutinin of the virus strain A/Anhui/1/2005 (H5N1), and wherein the composition induces antibody titers that neutralize heterologous H5N1 clades 4.0 and 7.0.

2. The composition of claim 1, wherein each of the first, second and third immunogenic agents comprises a full length hemagglutinin.

3. The composition of claim 1, wherein each of the first, second and third immunogenic agents comprises a nucleic acid encoding a full length hemagglutinin.

4. A method for inducing an immune response to an influenza virus in a subject comprising administering a prophylactically effective amount of the composition of claim 1 to a subject.

5. A method for treating or preventing an influenza virus infection comprising administering the composition of claim 1 to a subject.

6. The method of claim 4, wherein each of the first, second and third immunogenic agents comprises a full length hemagglutinin.

7. The method of claim 4, wherein each of the first, second and third immunogenic agents comprises a nucleic acid encoding a full length hemagglutinin.

8. The method of claim 5, wherein each of the first, second and third immunogenic agents comprises a full length hemagglutinin.

9. The method of claim 5, wherein each of the first, second and third immunogenic agents comprises a nucleic acid encoding a full length hemagglutinin.

10. The composition of claim 1, wherein the composition further induces antibody titers that neutralize heterologous H5N1 clades 1.0, 2.1, 2.2, and 8.0.

* * * * *